United States Patent
Riley et al.

(10) Patent No.: US 8,011,125 B2
(45) Date of Patent: Sep. 6, 2011

(54) BUSINESS FORM AND SELF-LAMINATING WRISTBAND WITH OVERLAPPING LAMINATION PANELS

(75) Inventors: James M. Riley, Saint Louis, MO (US); Sanjay K. Jain, Saint Louis, MO (US); Mark Greer, O'Fallon, MO (US); Richard E. Feiner, Jackson, MO (US)

(73) Assignee: Laser Band, LLC, St. Louis, MO (US)

( * ) Notice: Subject to any disclaimer, the term of this patent is extended or adjusted under 35 U.S.C. 154(b) by 0 days.

(21) Appl. No.: 12/847,271

(22) Filed: Jul. 30, 2010

(65) Prior Publication Data

US 2011/0000114 A1 Jan. 6, 2011

Related U.S. Application Data

(63) Continuation of application No. 11/203,601, filed on Aug. 12, 2005, now Pat. No. 7,779,569, which is a continuation-in-part of application No. 10/627,135, filed on Jul. 25, 2003, now Pat. No. 7,017,294, which is a continuation-in-part of application No. 10/283,777, filed on Oct. 30, 2002, now Pat. No. 7,017,293, which is a continuation-in-part of application No. 10/256,758, filed on Sep. 27, 2002, now Pat. No. 7,047,682.

(51) Int. Cl.
*A44C 5/00* (2006.01)
(52) U.S. Cl. .............. 40/633; 40/665; 283/75
(58) Field of Classification Search .......... 40/633, 40/665; 283/75
See application file for complete search history.

(56) References Cited

U.S. PATENT DOCUMENTS

| | | |
|---|---|---|
| 230,455 A | 7/1880 | Wilcox |
| 919,983 A | 4/1909 | Walsh |

(Continued)

FOREIGN PATENT DOCUMENTS

DE 202009015077 U1 1/2010

(Continued)

OTHER PUBLICATIONS

"Yes, Sir, That's My Baby!," Material Management in Health Care, Feb. 1999, vol. 8, No. 2, Health Forum, Inc.

(Continued)

*Primary Examiner* — Joanne Silbermann
(74) *Attorney, Agent, or Firm* — Thompson Coburn LLP

(57) ABSTRACT

A business form including a wristband is provided with a print area forming a badge, the badge having a length less than and a width greater than a width of either of two straps used to attach the wristband to the wrist, the badge thus having a greater print area to improve the readability of the indicia displayed therein. A business form including a wristband has a bulged rectangularly shaped print area to allow information to be printed transversely across the print area to improve readability of the indicia displayed in the print area. Thus, the bulged rectangularly shaped print area can accommodate one or both of bar codes printed thereon in ladder as well as picket fence fashion. A security seal is disclosed which comprises a small, adhesive coated patch of laminate for sealing the joinder of the wristband ends and which has points of weakness such as X's die cut therein so that it separates or destructs upon removal to provide an indication of tampering with the wristband. Also disclosed is an embodiment of the wristband form that is imprinted with identifying indicia for collecting, tracking and administering a patient's blood collection and blood product compatibility.

55 Claims, 23 Drawing Sheets

U.S. PATENT DOCUMENTS

| | | | |
|---|---|---|---|
| 922,948 A | 5/1909 | Portmore |
| 1,383,335 A | 7/1921 | Penksa |
| 1,517,456 A | 12/1924 | Pulliam |
| 2,054,227 A | 9/1936 | Nichols |
| 2,073,280 A | 3/1937 | Lederer |
| 2,553,676 A | 5/1951 | Roos |
| 2,641,074 A | 6/1953 | Richmond |
| 2,687,978 A | 8/1954 | Vogt |
| 2,914,166 A | 11/1959 | Bihler |
| 3,153,869 A | 10/1964 | Twentier |
| 3,197,899 A | 8/1965 | Twentie |
| 3,402,808 A | 9/1968 | Yannuzzi |
| 3,517,802 A | 6/1970 | Petrie |
| 3,585,743 A | 6/1971 | Jeffers |
| 3,660,916 A | 5/1972 | McDermott et al. |
| 3,854,229 A | 12/1974 | Morgan |
| 4,004,362 A | 1/1977 | Barbieri |
| 4,078,324 A | 3/1978 | Wiebe |
| 4,179,833 A | 12/1979 | Knodel |
| 4,226,036 A | 10/1980 | Krug |
| 4,233,715 A | 11/1980 | McDermott |
| 4,370,370 A | 1/1983 | Iwata et al. |
| 4,565,731 A | 1/1986 | Komatsu et al. |
| 4,612,718 A | 9/1986 | Golub et al. |
| 4,627,994 A | 12/1986 | Welsch |
| 4,630,384 A | 12/1986 | Breen |
| 4,682,431 A | 7/1987 | Kowalchuk et al. |
| 4,696,843 A | 9/1987 | Schmidt |
| 4,783,917 A | 11/1988 | Smith et al. |
| 4,829,604 A | 5/1989 | Allen et al. |
| 4,854,610 A | 8/1989 | Kwiatek |
| 4,855,277 A | 8/1989 | Walter |
| 4,914,843 A | 4/1990 | DeWoskin |
| 4,941,210 A | 7/1990 | Konucik |
| 4,950,638 A | 8/1990 | Yuyama et al. |
| 4,956,931 A | 9/1990 | Selke |
| D312,654 S | 12/1990 | Giordano |
| 4,978,144 A | 12/1990 | Schmidt et al. |
| 4,991,337 A | 2/1991 | Solon |
| RE33,616 E | 6/1991 | Welsch |
| 5,026,084 A | 6/1991 | Pasfield |
| 5,045,426 A | 9/1991 | Maierson et al. |
| 5,135,789 A | 8/1992 | Schmidt |
| 5,222,823 A | 6/1993 | Conforti |
| 5,227,004 A | 7/1993 | Belger |
| 5,227,209 A | 7/1993 | Garland |
| 5,283,969 A | 2/1994 | Weiss |
| 5,311,689 A | 5/1994 | Lindsey |
| 5,318,326 A | 6/1994 | Garrison |
| 5,331,140 A | 7/1994 | Stephany |
| 5,351,993 A | 10/1994 | Wright et al. |
| 5,370,420 A | 12/1994 | Khatib et al. |
| 5,381,617 A | 1/1995 | Schwartztol et al. |
| 5,383,686 A | 1/1995 | Laurash |
| 5,395,667 A | 3/1995 | Ohno et al. |
| 5,401,110 A | 3/1995 | Neeley |
| 5,418,026 A | 5/1995 | Dronzek, Jr. et al. |
| 5,427,416 A | 6/1995 | Birch et al. |
| 5,486,021 A | 1/1996 | Laurash |
| 5,486,436 A | 1/1996 | Lakes |
| 5,509,693 A | 4/1996 | Kohls |
| 5,509,694 A | 4/1996 | Laurash et al. |
| 5,518,787 A | 5/1996 | Konkol |
| 5,524,934 A | 6/1996 | Schwan et al. |
| 5,547,227 A | 8/1996 | Laurash et al. |
| 5,560,657 A | 10/1996 | Morgan |
| 5,581,924 A | 12/1996 | Peterson |
| 5,586,788 A | 12/1996 | Laurash |
| 5,595,404 A | 1/1997 | Skees |
| 5,596,202 A | 1/1997 | Arakawa |
| 5,598,970 A | 2/1997 | Mudry et al. |
| 5,601,222 A | 2/1997 | Haddad |
| 5,601,313 A | 2/1997 | Konkol et al. |
| 5,630,627 A | 5/1997 | Stewart |
| 5,637,369 A | 6/1997 | Stewart |
| 5,648,143 A | 7/1997 | Mehta et al. |
| 5,653,472 A | 8/1997 | Huddleston et al. |
| 5,662,976 A | 9/1997 | Popat et al. |
| 5,670,015 A | 9/1997 | Finestone et al. |
| 5,687,903 A | 11/1997 | Akridge et al. |
| D391,991 S | 3/1998 | Conner |
| 5,765,885 A | 6/1998 | Netto et al. |
| 5,785,354 A | 7/1998 | Haas |
| 5,842,722 A | 12/1998 | Carlson |
| 5,877,742 A | 3/1999 | Klink |
| 5,933,993 A | 8/1999 | Riley |
| 5,984,363 A | 11/1999 | Dotson et al. |
| 6,000,160 A | 12/1999 | Riley |
| 6,006,460 A | 12/1999 | Blackmer |
| 6,016,618 A | 1/2000 | Attia et al. |
| D423,044 S | 4/2000 | Burke et al. |
| 6,053,535 A | 4/2000 | Washburn et al. |
| 6,055,756 A | 5/2000 | Aoki |
| 6,058,639 A | 5/2000 | Tinklenberg et al. |
| 6,067,739 A | 5/2000 | Riley |
| 6,071,585 A | 6/2000 | Roth |
| 6,092,321 A | 7/2000 | Cheng et al. |
| 6,108,876 A | 8/2000 | Hubbert |
| 6,155,476 A | 12/2000 | Fabel |
| 6,155,603 A | 12/2000 | Fox |
| 6,159,570 A | 12/2000 | Ulrich et al. |
| 6,199,730 B1 | 3/2001 | Chisolm |
| D448,404 S | 9/2001 | Hamilton et al. |
| 6,303,539 B1 | 10/2001 | Kosarew |
| 6,331,018 B1 | 12/2001 | Roth et al. |
| 6,343,819 B1 | 2/2002 | Shiozaki |
| 6,361,078 B1 | 3/2002 | Chess |
| 6,364,366 B1 | 4/2002 | Schwartz |
| 6,409,871 B1 | 6/2002 | Washburn et al. |
| 6,438,881 B1 | 8/2002 | Riley |
| 6,510,634 B1 | 1/2003 | Riley |
| 6,517,921 B2 | 2/2003 | Ulrich et al. |
| D473,264 S | 4/2003 | Sanford et al. |
| 6,611,962 B2 | 9/2003 | Redwood et al. |
| 6,641,048 B1 | 11/2003 | Schintz et al. |
| 6,685,228 B2 | 2/2004 | Riley |
| 6,748,687 B2 | 6/2004 | Riley |
| 6,782,648 B1 | 8/2004 | Mosher, Jr. |
| 6,807,680 B2 | 10/2004 | Sloot |
| 6,836,215 B1 | 12/2004 | Laurash et al. |
| 6,844,041 B2 | 1/2005 | Squier et al. |
| D503,197 S | 3/2005 | Stewart et al. |
| 6,863,311 B2 | 3/2005 | Riley |
| 6,971,200 B2 | 12/2005 | Valenti, Jr. |
| 7,017,293 B2 | 3/2006 | Riley |
| 7,017,294 B2 | 3/2006 | Riley |
| D521,565 S | 5/2006 | Stewart et al. |
| 7,047,682 B2 | 5/2006 | Riley |
| 7,197,842 B2 | 4/2007 | Ali |
| 7,222,448 B2 | 5/2007 | Riley |
| 7,240,446 B2 | 7/2007 | Bekker |
| 7,286,055 B2 | 10/2007 | Girvin et al. |
| 7,523,576 B1 | 4/2009 | Petty |
| D611,984 S | 3/2010 | Ali et al. |
| 7,763,344 B2 | 7/2010 | Riley et al. |
| 7,779,569 B2 | 8/2010 | Riley et al. |
| 7,779,570 B2 | 8/2010 | Riley |
| 7,784,209 B2 | 8/2010 | Greer |
| 7,784,210 B2 | 8/2010 | Riley et al. |
| 7,818,908 B2 | 10/2010 | Greer |
| 7,823,310 B2 | 11/2010 | Jain et al. |
| 7,877,915 B2 | 2/2011 | Jain et al. |
| 7,883,018 B2 | 2/2011 | Riley et al. |
| 7,918,045 B2 | 4/2011 | Riley |
| 2002/0152928 A1 | 10/2002 | Lawandy et al. |
| 2002/0176973 A1 | 11/2002 | Keiser |
| 2003/0001381 A1 | 1/2003 | Riley |
| 2003/0003249 A1 | 1/2003 | Benim et al. |
| 2003/0011190 A1 | 1/2003 | Ryan |
| 2004/0060216 A1 | 4/2004 | Riley |
| 2004/0068906 A1 | 4/2004 | Riley |
| 2004/0128892 A1 | 7/2004 | Valenti |
| 2004/0148836 A1 | 8/2004 | Riley |
| 2004/0244251 A1 | 12/2004 | Riley |
| 2005/0091896 A1 | 5/2005 | Kotik et al. |
| 2005/0108912 A1 | 5/2005 | Bekker |
| 2005/0279001 A1 | 12/2005 | Riley |

| | | | |
|---|---|---|---|
| 2005/0281989 | A1 | 12/2005 | Finger |
| 2006/0230661 | A1 | 10/2006 | Bekker |
| 2006/0236578 | A1 | 10/2006 | Saint et al. |
| 2006/0242875 | A1 | 11/2006 | Wilson et al. |
| 2006/0261958 | A1 | 11/2006 | Klein |
| 2007/0089342 | A1 | 4/2007 | Jain et al. |
| 2007/0120358 | A1 | 5/2007 | Waggoner et al. |
| 2007/0243361 | A1 | 10/2007 | Riley et al. |
| 2007/0257113 | A1 | 11/2007 | Davis et al. |
| 2008/0098636 | A1 | 5/2008 | Greer |
| 2009/0031602 | A1 | 2/2009 | Riley |
| 2009/0094872 | A1 | 4/2009 | Ali et al. |
| 2009/0094873 | A1 | 4/2009 | Riley |
| 2009/0193701 | A1 | 8/2009 | Greer |
| 2009/0277061 | A1 | 11/2009 | Jain et al. |
| 2009/0282717 | A1 | 11/2009 | Jain et al. |
| 2010/0071241 | A1 | 3/2010 | Jain et al. |
| 2010/0253060 | A1 | 10/2010 | Riley et al. |
| 2010/0281724 | A1 | 11/2010 | Greer et al. |

FOREIGN PATENT DOCUMENTS

| | | | |
|---|---|---|---|
| EP | 1039431 | | 9/2000 |
| EP | 1974603 | A2 | 10/2008 |
| FR | 2806594 | A | 9/2001 |
| GB | 960859 | | 6/1964 |
| GB | 2045718 | | 11/1980 |
| GB | 2160492 | | 12/1985 |
| GB | 2228915 | A | 9/1990 |
| JP | 63175913 | A | 11/1988 |
| JP | 5-61777 | | 8/1993 |
| JP | 08-190350 | | 7/1996 |
| JP | 08299035 | A | 11/1996 |
| JP | 3032299 | | 12/1996 |
| JP | 10-207374 | | 8/1998 |
| JP | 11015383 | A | 1/1999 |
| JP | 2001316921 | A | 11/2001 |
| JP | 2002117190 | A | 4/2002 |
| JP | 2002351321 | A | 12/2002 |
| JP | 2003066849 | | 3/2003 |
| JP | 2003157010 | | 5/2003 |
| JP | 2003164307 | | 6/2003 |
| JP | 2006039209 | | 2/2006 |
| WO | 95/02877 | | 1/1995 |
| WO | 96/12618 | | 5/1996 |
| WO | 98/23081 | | 5/1998 |
| WO | 99/18817 | | 4/1999 |
| WO | 02/39412 | | 5/2002 |
| WO | 03/003331 | | 1/2003 |
| WO | 2004/028826 | | 4/2004 |
| WO | 2005/064574 | | 7/2005 |
| WO | 2006/007356 | | 1/2006 |
| WO | 2007/021375 | | 2/2007 |
| WO | 2007/133906 | | 11/2007 |
| WO | 2008/079952 | A2 | 7/2008 |
| WO | 2009099787 | A1 | 8/2009 |
| WO | 2009/137195 | | 11/2009 |
| WO | 2010129131 | | 11/2010 |

OTHER PUBLICATIONS

Avery Laminated Identification Cards #5361.
Avery Dennison DuraCard.
Brochure entitled: "Integrated Document Management Software"; Smead Manufacturing Company; Date Unknown; Form No. SLI-95.
Brochure entitled: "Color-Bar a Folders"; Smead Manufacturing Company; Date Unknown.
Brochure entitled: "Color-Bara—Click Stripa Labeling System"; Smead Manufacturing Company; Date Unknown; Form No. SSS-CS-00.
Catalog entitled: "Reseller Catalog Number One"; Smead Software Solutions ; Date Unknown; Form No. SSS-RC1-00.
Disaster Management Systems, Inc., Triage Tag, Copyright 1996, Pomona, California.
Gretchen Berry, "Wrist Watch," Advance for Healthcare Information Professionals, Feb. 15, 1999.
ID Warehouse (http://web.archive.org/web/20050131235601/http://idwarehouse.com/) Jan. 31, 2005. p. 1: WB1908, Stock Vinyl Wristband.
International Preliminary Report on Patenability (Chapter II) for PCT/US2009/031979 issued May 21, 2010.
International Preliminary Report on Patentability (Chapter I) for PCT/US2008/064972 dated Dec. 1, 2009.
International Preliminary Report on Patentability (Chapter II) for PCT/US2008/059616 dated Jul. 14, 2009.
International Preliminary Report on Patentability (Chapter II) for PCT/US2009/039183 issued Apr. 20, 2010.
International Search Report and Written Opinion for PCT/US2010/030361 dated Jul. 16, 2010.
International Search Report for PCT/US2009/031979 dated Mar. 9, 2009.
International Search Report for PCT/US2009/039183 dated Jun. 25, 2009.
Maryland Department of Transportation, Maryland Emergency Medical Services, Triage Tag, Copyright MIEMMS 1999, Maryland.
Patent Cooperation Treaty; Partial International Search Report; May 24, 2005.
Patent Cooperation Treaty; Partial International Search Report; Sep. 13, 2004.
Posey Movable I.D. Bracelet; downloaded from http:/www.posey.com/products/4648.html on Aug. 18, 2004.
Sample of Standard Register Label.
Sample of Standard Register Labels.
Standard Register, P.S. Magazine, Fall 1998, Dayton, Ohio.
Office Action for CA Application 2567762 dated Apr. 11, 2011.
Office Action for CN Application 200680035179.8 dated Apr. 1, 2011.
Office Action for EP Application 03773060.3 dated Apr. 6, 2011.
Office Action for U.S. Appl. No. 11/373,923 dated May 17, 2011.
Office Action for U.S. Appl. No. 12/115,945 dated Jun. 2, 2011.
International Preliminary Report on Patentability (Chapter II) for PCT/US2010/030361 issued May 13, 2011.

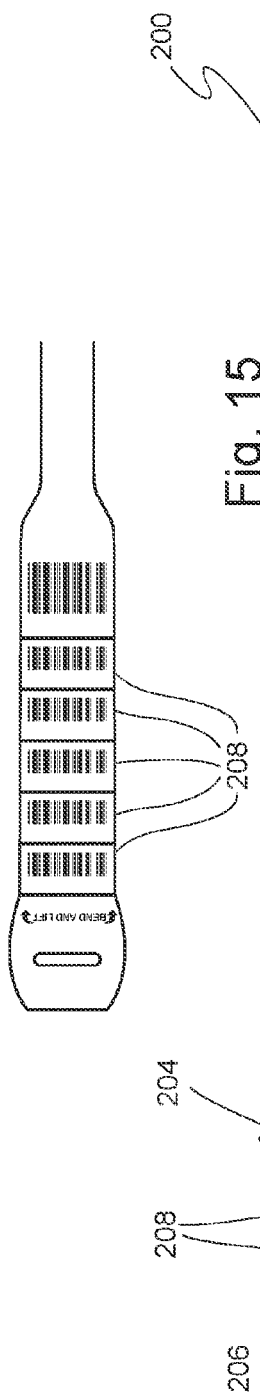
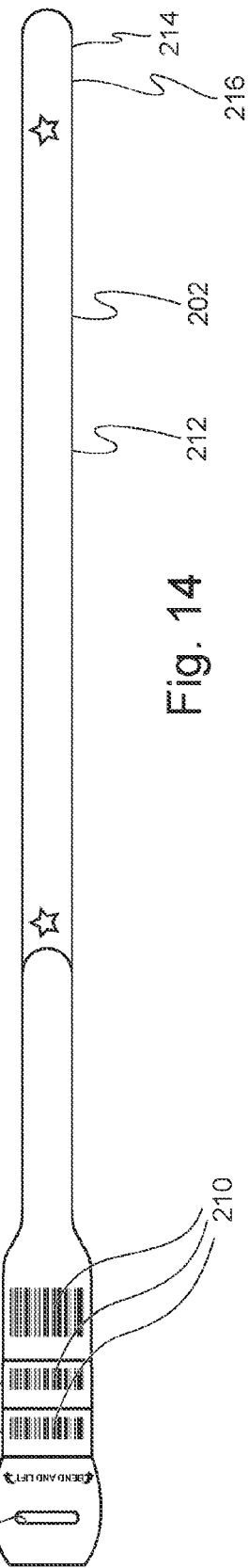
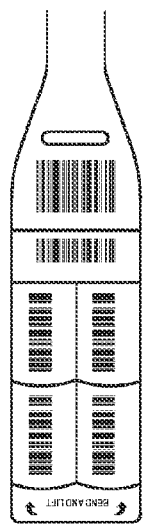
Fig. 14
Fig. 15
Fig. 16
Fig. 17

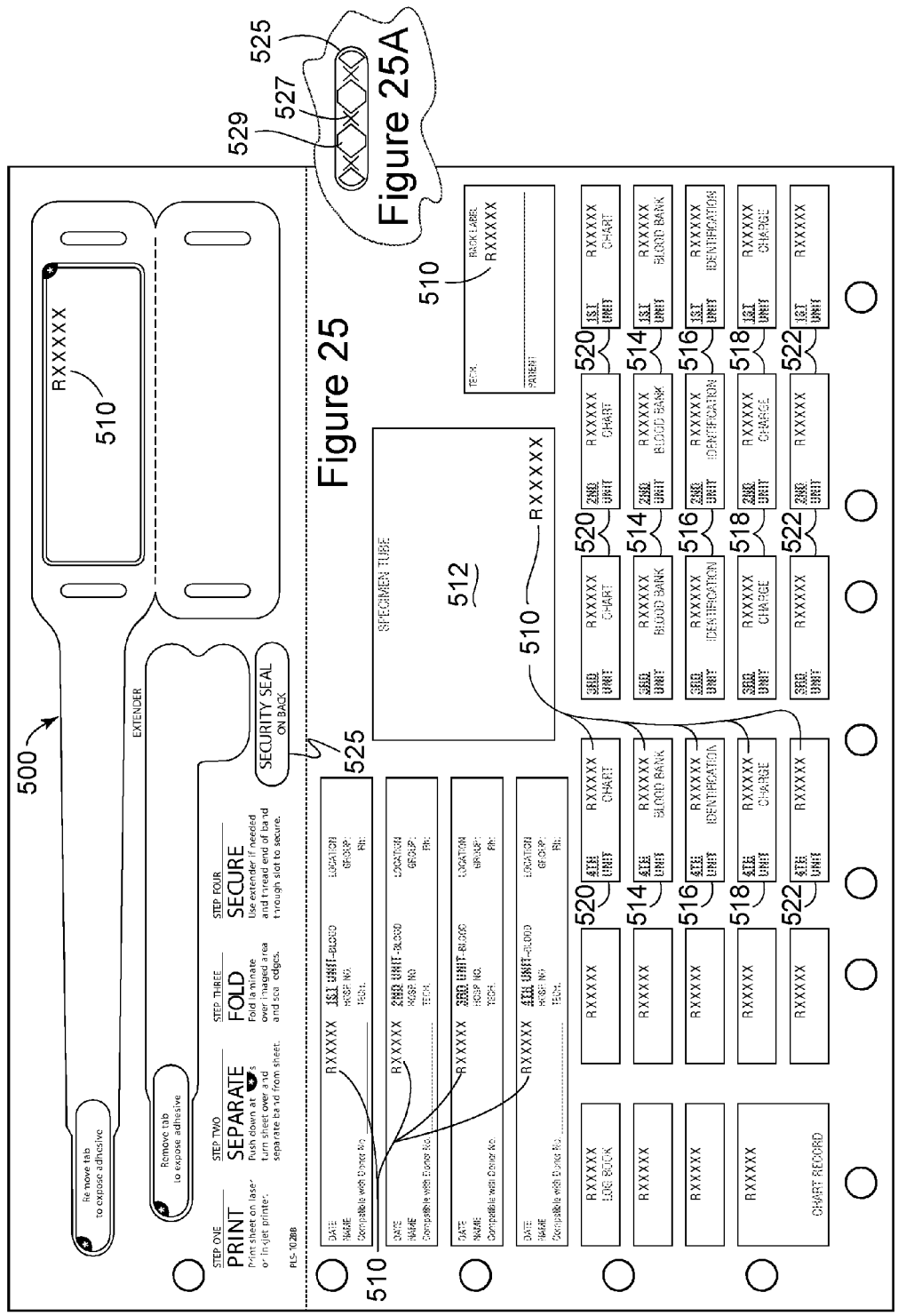

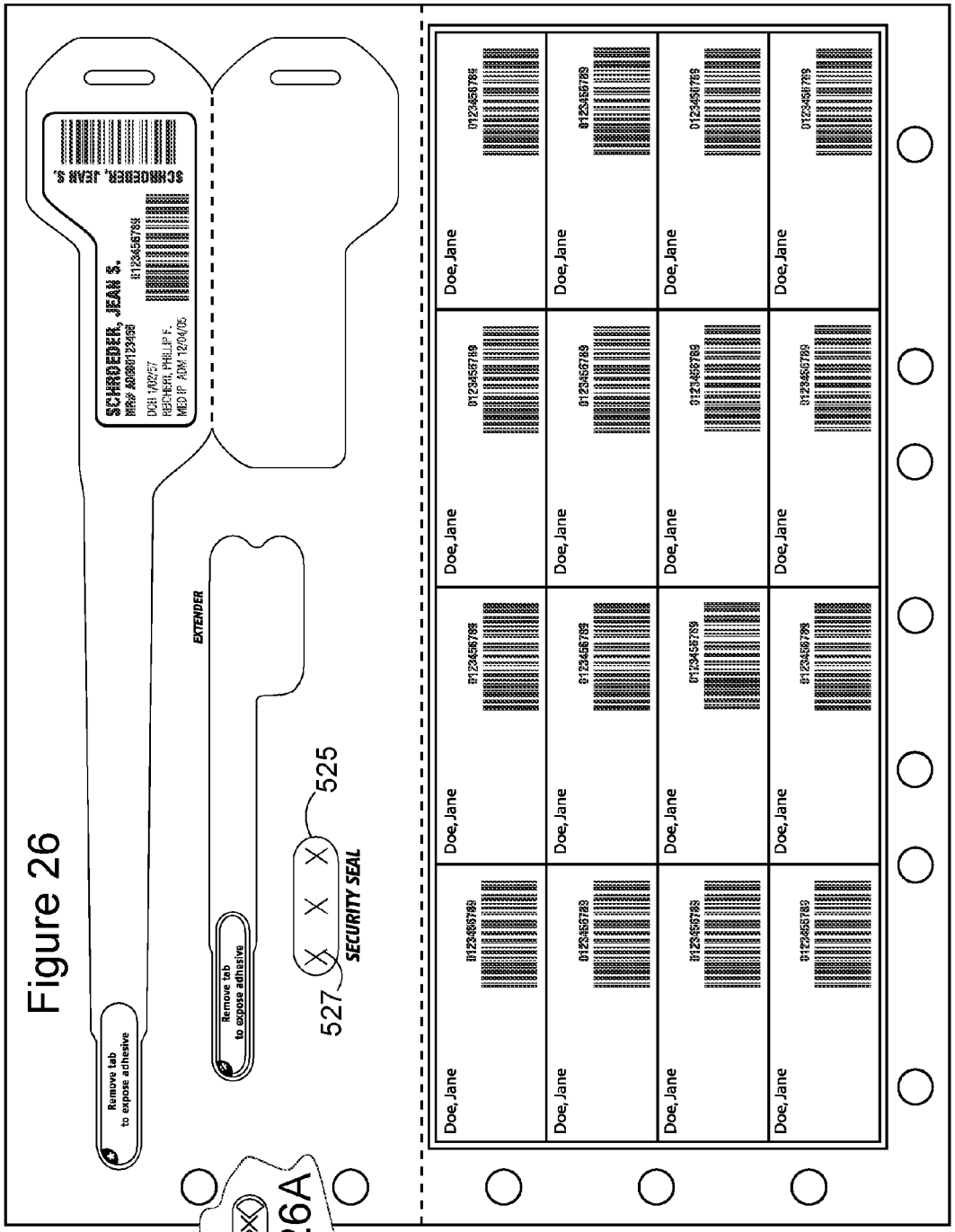

BUSINESS FORM AND SELF-LAMINATING WRISTBAND WITH OVERLAPPING LAMINATION PANELS

CROSS REFERENCE TO RELATED APPLICATION

This patent application is a continuation of application Ser. No. 11/203,601, which was filed on Aug. 12, 2005, which is a continuation-in-part of application Ser. No. 10/627,135, which was filed on Jul. 25, 2003 now U.S. Pat. No. 7,017,294, issued Mar. 28, 2006, which is a continuation-in-part of application Ser. No. 10/283,777, which was filed on Oct. 30, 2002 now U.S. Pat. No. 7,017,293, issued Mar. 28, 2006, which is a continuation-in-part of application Ser. No. 10/256,758 filed Sep. 27, 2002 now U.S. Pat. No. 7,047,682, issued May 23, 2006.

BACKGROUND AND SUMMARY OF THE INVENTION

There are many situations where it would be convenient to have available a way to separately identify a person, such as a health care patient, with his/her possessions or other related items with which the person needs to be associated. As this is written, the recent events of the tragedy of Sep. 11, 2001 have provided a glaring example of one such situation. In that situation, it became evident that there was no convenient way to associate people desperately in need of health care with their belongings. Even more horrifying was the need to identify body parts, tag them, and assemble some kind of data base that could be used to sort through the confusion and chaos created on that terrible day. Under those circumstances, and many other similar emergency circumstances, the health care workers and the emergency workers are under tremendous time pressure, with protective clothing such as gloves being used to avoid personal danger to themselves, to sort through what is presented to them in the way of victims needing medical attention, their possessions including valuables, and a need to communicate with their family. The environment is usually hostile, with what may be fire, flying debris, collapsing buildings, un-breathable air, etc. which makes it quite different from a usual hospital or other controlled environment and makes handling any "standard" form imminently more difficult.

Another aspect to the situation that must be considered is that it is not uncommon for different care takers to handle a single victim. Generally, when a victim is first attended, he is categorized for the nature and extent of his injuries. Then, in those situations where there is a mis-match between the number of victims and the number of medical personnel, the most severely injured are attended to first and the remainder are treated as time becomes available. This is routine, and an attempt to minimize loss of life in what can be a desperate situation. Thus, it is commonly required to "triage" the victims, and then identify them in some way that makes it immediately apparent to medical workers just what their medical situation is. This sounds easy, but in the chaos of these situations, even with medical personnel who are well trained, there can be lost time in this process and if a good strategy is not used for this classifying, victims can be mis-identified or their status not readily ascertainable after classification, so that the precious time of these "angels of mercy" can be needlessly wasted as they move from one victim to another.

This type of emergency situation creates needs that are unique, beyond the needs of a form intended for use in a clean environment available in an emergency room. As mentioned, medical personnel are usually wearing gloves and in a hurry. Thus, any form that would be used must be adapted to be easily handled with clumsy fingers. There is no time for instruction, so the form must be virtually intuitive for use. There are commonly fluids present, unfortunately most often blood and other body fluids, so the form must be protected. There needs to be a simple, fast, fool-proof way to apply the form to the victim, and his possessions, with a reliable way to link them together. There is a further need to be able to quickly collect the identifying information from the form as it is attached to a victim so he may be processed quickly and the information accurately collected. The identifying information commonly needs to be thought out in advance, and might even be pre-coded to mesh with the triage operation so that merely knowing the identifying information conveys some information about victim medical status. And, there is desirably some flexibility available in use of the form to accommodate different victim conditions.

Still another need exemplified by this tragedy is that of providing information to families and other loved ones. After the 9/11 event, it was well publicized that family members and others resorted to walking the streets, following any rumor, visiting geographically separated emergency medical care sites, asking for information if not finding their loved one. This itself caused much anxiety and pain amongst the survivors. While not as critical as getting information about survivors to their families, this inability to assemble information created other problems including the inability to gauge the magnitude of the tragedy. A complete list of the survivors was impossible to assemble for days, even though information was individually available by then. There just was not a convenient way to assemble this information in a common data base. Some attempts were made to use the internet, but inaccuracies abounded and the information posted there was soon being ignored, at least partly due to the lack of confidence in that information.

To solve these and other needs in the prior art, the inventor herein has previously developed a business form as disclosed and claimed in one of the parents in several embodiments and a method incorporating the use of that form that have particular application to these kind of medical emergency situations. Briefly, a first embodiment of the form comprises a carrier sheet of paper stock, with a wristband/label assembly die cut thereinto for separation from the carrier sheet. The paper stock is preferably pre-printed with identifying indicia, color coded and covered top and bottom with a layer of protective coating which may preferably be a poly plastic. The wristband/label assembly may be dry adhered to a bottom layer of a carrier film so that it may be readily separated from the carrier without retaining any adhesive. The wristband portion of the assembly may have a tab on one end and a long strap portion which, to be assembled, is wrapped around an object such as a victim's wrist, looped back through a "cinch" comprising a slot in the tab and then adhered to itself by an adhesive portion at the end of the strap portion. The tab preferably has a plurality of individually separable labels die cut thereinto, with each of the labels and the wristband having an identifying indicia which may preferably be a bar code. In the embodiment disclosed in one of the parent applications, the slot is inboard of the labels while in the embodiment first disclosed herein the slot is outboard of the label carrying portion of the tab. Furthermore, the embodiment first disclosed herein is narrower, more streamlined, and eliminates the medical indicia making the wristband/label form more universally applicable as a simple identifier. Some of the other embodiments first disclosed herein include the narrower, single ply, non-laminated strap portion while relying on adhesive coated tabs to secure the wristband about the wrist.

In use, the wristband/label assembly of the parent is separated from the carrier, carrying the tab filled with labels, and the strap portion. The cinch slot is die cut and formed as the assembly is separated with its filler piece adhered to remain behind with the bottom film carrier sheet. The strap portion has its end covered with a laminated bottom patch so that as it separates it carries with it a peel away covering over its end having the adhesive. After being separated from the carrier, the wristband/label assembly has a protective layer over both its top and bottom for resisting fluid contamination and the tab has a label section which may be perforated for separation from the wristband. Each of the labels are individually separable and carry the identifying indicia. The wristband may preferably be color coded, and the forms may be made in sets with multiple ones of each of a number of different colors. Alternately, color coded, perforated tabs may be provided at the end of the tab portion, such that the medical technician need only separate one or more tabs, leaving as the outside tab the correct one to visually indicate the condition of the victim. A blank tab is preferably provided at the very edge of the tab portion so that no one would mistakenly interpret the failure to separate a tab as a conscious attempt at indicating medical condition. In still another embodiment, the medical indicia may be eliminated and the strap portion streamlined to allow for a more generic use of the form for merely indicating identity of the patient or other individual for other purposes than medical. The wristband may be readily applied by wrapping the strap portion about the person's appendage, slipping it through the "cinch" comprising the slot to tighten it about the appendage, pulling it tight, and then folding the strap portion back onto itself for attachment with the adhesive after removing the peel away covering.

In a second embodiment as shown and described in one of the parent applications hereto, the wristband/label assembly is pre-printed and formed in its final configuration, with a tab/label portion and a strap portion made from preferably four layers. A top, clear film layer overlies and protects a face stock layer upon which the pre-printed information including bar codes and color "condition" codes are applied. A layer of adhesive then joins the face stock to a base film material, again to protect the face stock in use. In either embodiment, more than one slot, or "cinch" point, may be provided to allow for a snug fit to different sized body parts. Also, more or fewer bar coded labels, of smaller or larger size, may be selected for use to suit a designer's preferences or user's needs. And, as explained above, the slot may be outboard of the label portion, thereby making the wristband easier to attach to a person, and without sacrificing integrity as the underlying web provides more than adequate strength for maintaining the wristband in its intended use.

In the method of the parent invention, once a form has been applied to a victim, and the victim thus associated with an identifying indicia, and his possessions properly tagged, software pre-loaded into a computer may then receive as much information about the victim as is available. Items of information might include his associated color code (which would preferably be indicative of his medical condition), his name and other demographic information, his statistics such as height, weight, race, etc., more detailed information as to the nature of his injuries or condition, the location where this victim is processed, and other appropriate information. The computer may then go on-line, or be on-line, and the data set up-linked to a web site. A plurality of treatment centers could each be simultaneously processing victims, and transmitting data to the web site for ready access and display to anyone interested in learning about a victim's condition. As a victim's condition changes, updated information could be provided to the web site, although it is considered by the inventor that the method of the parent is most effective in providing early information as fast as possible to the most people. Updated information could be available more directly as a victim's family locates and goes to where treatment is being given. Security in the web site and data links would prevent any mischief from occurring which might compromise the integrity of the data such that families could rely on the information posted.

As can be appreciated by those of ordinary skill in the art, there is unfortunately need for the parent invention given the heightened risk of terrorism that the world now faces, and along with that arises an increased need to facilitate not only the quick processing of victims but also the task of collecting and disseminating information about these victims. The parent invention addresses these needs, which in actuality are long felt needs exacerbated by our changing times. Accordingly, the foregoing provides a brief description of some of the advantages and features of the parent invention. A fuller understanding may be attained by referring to the drawings and description of the preferred embodiment of the parent which follow for the readers understanding.

The inventor has taken several of the features of the parent invention and used it to build onto his prior work in the wristband art as exemplified by the following patents issued to the inventor herein, the disclosures of which are incorporated herein by reference: U.S. Pat. Nos. 6,438,881; 6,067,739; 6,000,160; and others still pending. In his invention as disclosed and claimed in the more recently filed second patent application referenced above, he has incorporated the "cinch" of the parent into a self laminating wristband form in a unique and non-obvious way to provide many advantages and features not hereto available. Although the second parent's invention is exemplified in several embodiments as explained in greater detail below, each of which has its own unique advantages and features, it represents a departure from the construction found in the inventors prior patents. Some of the differences include the use of a single, preferably narrow, strap portion extending generally from one side of the face stock region, with the cinch comprising a slot located on either side of the face stock and either adjacent the top or bottom portion of the laminating portion that overlies the face stock. With this construction, it is thought that several advantages are obtained over the wristband construction of his prior inventions. First, in this invention the inventor uses less face stock resulting in a smaller area of the form needing to be over-laminated. In other words, in the inventor's prior patented wristbands, virtually the entire length of the wristband comprised face stock, all of which was over-laminated. In the more recent parent invention, preferably only a "patch" of face stock is used which does reduce the amount of space for printing but which at the same time reduces the size of the over-lamination "patch" needed. This smaller over-lamination "patch" is much easier for a nurse or other medical professional to fold over and complete the assembly, and thus apply the wristband to the patient. A related advantage is that by eliminating the face stock from the "strap portion" that surrounds the patient's wrist, this strap portion may be narrower and formed from a single layer of the lamination (with no adhesive applied). This is more comfortable to the patient for several reasons. The strap is narrower, thereby being less likely to bind or press into the patient's skin as he moves his wrist in doing daily living activities. The strap is also thinner as it is formed from only a single layer and may thus be more flexible. In this construction, a thinner laminate may be used than in prior designs which increases the patient's comfort. Patient comfort is an important consideration as patient's in hospitals are generally uncomfortable to begin with, being out of their ordinary environment, and those in need of hospital care are generally infirm, older or younger such as prenatal, and their skin may be more sensitive than normal. So, this is an important design criteria.

Still another advantage comes through incorporation of the cinch in this design. The cinch preferably comprises a slot which may be located in one of several places in the wristband, but it offers several unique advantages. First, if need be, the cinch may be used to more easily apply the wristband to a patient as it gives the nurse a ready attachment fixture with which he/she is quite familiar, it being much like an ordinary belt worn by almost everyone, male and female. For those patients who may be uncooperative or thrashing about or otherwise resistive, applying the wristband amounts to getting the strap through the slot and after that is achieved the rest needed to be done is relatively simple. For those patients who need to be tightly banded, the cinch provides a ready means to tighten down the strap and keep it tight while the cinch and strap are adhered in place. This allows for a simpler built in adjustment in strap length than with the prior designs. The cinch may be located in one of several places in the band, and each location offers its own unique advantages. If located intermediate the face stock and the strap, the face stock is converted into a "hang tag" which hangs freely from the patient's wrist after it is applied. This aids the nurse in finding and reading the information printed on the face stock, and also makes it easier for her to read imprinted indicia on the face stock with a hand held bar code reader, for example, as the surface is flat. Also, with this arrangement, a smaller strap is readily provided for smaller wrists such as with new-born babies. If the slot is located outboard from the face stock, the face stock hugs the patient's wrist much more like a conventional wristband, and an extra area of fold over laminate may be used to adhere the strap in place, making for a more secure attachment. Either arrangement would be desirable depending on the particular application, and is left to the user's choice.

As alluded to above, the strap portion is adhered in one of several ways, depending on the embodiment chosen. If the cinch is intermediate the face stock and strap, the end of the strap has a patch of adhesive which is used to adhere it back onto itself after being threaded through the slot. With the cinch outboard of the face stock, an "extension" of laminate is used which may carry adhesive along with a fold line through the slot so that after the strap is threaded through the slot the extension may be folded about the fold line and "clamp" the strap in place with adhesive. This provides a second means for adhering the strap in place.

The face stock layer has a printable region or ply defined therein with a die cut while the lamination layer has three elements die cut in to it. The lamination layer has a strap portion, a laminating portion, and a cinch portion all die cut therein, with adhesive being applied to preferably the extreme end of the strap portion for securing the strap to itself after the wristband has been applied, adhesive applied to the lamination portion to substantially, and preferably entirely, surround and enclose the face stock printable region, and adhesive applied to a cinch portion (if located outboard of the face stock) for adhering to the strap portion after it is passed through the cinch. Adhesive may preferably be omitted from the portion of lamination that overlies the face stock to improve it's readability, both visually and for bar coding. In variations to this embodiment, the cinch, which is preferably a slot aligned generally perpendicular to the face stock, may be located in one of several places, either outboard of the face stock region or intermediate the face stock and the strap portion. When positioned outboard of the face stock, the cinch may also be located in one of two places either in an extension of the lamination adjacent a top portion or the bottom portion of the lamination portion. When positioned intermediate the face stock and strap portion, the cinch may be formed from a pair of slots located in both the top and bottom portion of the lamination portion. In this arrangement, adhesive is applied to join the top and bottom lamination portions, but it does not aid in holding the strap in position unless the nurse takes the time and is able to obtain the cooperation of the patient to thread the strap through only one of the slots before folding the lamination halves together to enclose the face stock. However, this is thought to be a less desirable attachment arrangement than first enclosing the face stock and then threading the strap through the slot.

As an added feature, the inventor has previously developed an extender which is also formed in the same two plies of material, with the extender comprising a length of laminate having a fold over or "clamshell" portion with adhesive at one end, and a patch of adhesive at its opposite end. The extender is sized preferably to be of the same width as the strap portion and is applied to the strap portion by use of the clamshell which clamps onto the strap portion and along its length, with the extender patch of adhesive serving the function of joining the strap. With the extender, the wristband may be used with larger patient's, conveniently, without being limited to the overall length of the form or carrier in which the wristband is formed.

In variations of these embodiments previously disclosed in the parent applications, the wristband may be formed in a sheet with a plurality of self adhering, to peel off labels, all of which may be printed with identifying indicia or information relating to the patient. Several wristbands of different size, or the same size, may also be formed on a single sheet, with or without labels. The extender may also be provided in any one or more of the variations, which are only limited by the perceived needs of users, and design choice.

The parent applications disclosed forms that have been modified to provide even greater choice and advantage depending on the particular situation for which the wristband is needed. As an example, one form showed an arrangement where the cinch slot is outboard of the label portion, on a tab, and has eliminated the medical indicia thereby making the form more streamlined and suitable for use in a wider range of applications. Several arrangements for the label portion have also been shown as providing a variety of choices to suit different applications depending on the number of labels needed, and all without sacrificing the integrity of the form. As in other forms previously disclosed, bar coding or other means of identifying or numbering or segregating the forms have been shown.

With respect to the second general category of wristband forms, the inventor has provided a tab at an end adjacent the face stock area, with the tab having a second slot surrounded by adhesive and through which the tail or free end portion is inserted for joining the wristband about the person wearing it. After the free end is inserted, the slot is preferably folded over about a fold line, and the free end is captured and adhered in place. The remaining free end may then be inserted through the second slot and hidden beneath the face stock out of the way and less likely to be caught on something. This arrangement allows for the extra free end to be kept intact so that the wristband may later be re-adjusted in length by merely lifting the folded over tab and withdrawing the free end for re-positioning. As an added feature, the face stock is preferably extended to the edge of the outboard slot to thereby cover over the adhesive closest to where the free end slides through, thereby making it less likely to "hang up" on adhesive as the wristband is applied. Furthermore, as the adhesive is applied to the area surrounding the second slot, it need not be applied as a patch on the tip of the free end as in other embodiments disclosed in the parent applications. Thus, as the free end is inserted through the slot, there is no patch of adhesive to inadvertently grab a patient's skin or body hair again making this embodiment less likely to "hang up" on the patient as it is applied. Instead, the adhesive is placed on a surface facing away from the patient.

As disclosed in the parent applications, slots have been provided on each side of the face stock and through both of which the free end may be inserted. In this arrangement the face stock area overlies the free end, and the face stock area becomes less "rounded" than in other embodiments where only a single slot is used. This aids in reading the information placed on the face stock, and can be important in aiding this information should it be bar coded information. Also, with the two slot arrangement, the same form may be applied in different ways which enhances its versatility. This may be especially important for those applications where a single form may be intended to be used on different body parts of a patient. One such example is the Neo-natal, Intensive Care Unit (NICU) where wristbands are desirably applied not only to the leg but also the arm. In this application, the same wristband may be applied to different parts of the body, the leg and arm, and depending on size either one slot or both slots may be used to allow for patient comfort and ready accessibility to the imprinted information. However, even with the need to accommodate differently sized arms and legs, the same form may be used thereby minimizing inventory requirements and eliminating the waste or extra cost of using more than one sheet of wristbands.

The inventor has continued his work and developed several new embodiments of wristband forms, which draw upon the inventor's past designs and provide different arrangements and which in some instances will improve upon the readability of the print area so as to improve scanning and automated data input functions. One embodiment provides a change in the aspect ratio of the print area such that a laminated "badge" is created with a pair of narrower strap portions extending from the sides of the badge for attaching the wristband to the patient's wrist. This design may be achieved by either narrowing the width of the strap portions or by widening the face stock area which separates from the form, or the imaging area, or by doing some combination thereof. With this design, the imaging area may be enlarged to allow more information to be printed thereon, or to allow for an increased font size to enhance the readability of the information printed. With a smaller strap portion, the wristband may be more comfortable over wristbands with wider strap portions as well. By creating a "badge" for receiving the printed information, the wearer and any one wishing to access the printed information may more easily find the portion of the wristband containing the information due to its different and larger shape. In fact, in low level lighting, this different shape is even more useful for locating the information, and it is not uncommon for low level lighting conditions to exist as the patient is attended during the night. As the width is increased, a shorter length imaging area may be used and the imaging area may still receive and clearly display the patient information of interest. This reduced length imaging area allows the "badge" to be more naturally oriented on the top or bottom of a patient's wrist, and more likely lie flat against the wrist to thereby substantially reduce the curvature of the imaging area. This facilitates visual as well as automated reading of the indicia in the imaging area including, for instance, the scanning of bar codes. This same design is also provided in a less pronounced "badge" with a slimmer longer length imaging area version as well. Variations of this arrangement are also disclosed herein including forming the strap potions immediately to each side of the imaging area, providing a different silhouette for the different strap portions and especially at the transition from the imaging area, etc, as shown in the drawings and described below.

Another embodiment of the present invention provides enhanced readability of the print area with improved patient comfort by forming the imaging area or print area (typically face stock) with an enlarged portion, preferably located at one end of the usually rectangular shaped imaging or print area. "Rectangular shaped" or "rectangularly shaped" is intended to include rectangular, parallelogram, or similar shapes having two pairs of opposing sides with a longer dimension along one pair than another, but perhaps with rounded or shaped or angled corners for example, or a print area having an asymmetrical or a symmetrical configuration such as a square, or other approximately rectangular shape. This "bulged" area is preferably arranged as an enlarged width at one end of the generally rectangular imaging or print area, although it could be formed at any other location along the length thereof. In this arrangement, the imaging area preferably has a generally "L"-shape that accommodates the transverse printing of more information than with the simple rectangular print area. By printing information transversely across the print area, the information lies along the length of the arm as opposed to across the wrist and is thus more likely to lie fiat. When a bar code is used and printed on the bulged area, this flat orientation is expected to render the bar code more "readable" than if printed across the length of the imaging area. In the art, bar codes are commonly referred to as either "picket fence" when arranged to be read horizontally, and "ladder" when arranged to be read vertically. With the print or imaging area having a bulged rectangular shape, both or either of ladder or picket fence bar codes of a length commonly used in a health care application may be printed thereon and later reliably read with relative ease. This bulged rectangular construction is also designed with a bulged rectangular overlay to be self laminating and the wristband includes a cinch slot and strap for securing the wristband.

Other new embodiments include various new arrangements of the lamination layer and strap arrangements formed in the laminating layer. For example, the straps may be formed on the different halves of the imaging area over-lamination portion, instead of on the same half. Or, the straps may be both formed on the over-laminating half of the laminating layer. Still another new feature is the security seal which comprises a separate length of laminating layer which may be removed and applied to overlie the attachment point of the main straps. It provides a secondary seal and substantially secures the wristband, making it much more difficult for a patient to remove the wristband. Also, the security seal has a number of die cut X's in it so that once applied, its removal will likely result in it being torn apart or destructed. This destructed security seal is then visual evidence of a tampering with the wristband joinder and is an alert to a nurse that the patient has tampered with his identifying wristband and the nurse needs to re-verify the patient's identity before administering any medicine, providing treatment or taking patient parameters such as blood pressure, etc.

In another aspect of the present invention, the inventor has developed a form including a detachable, self-laminating wristband, and preferably a plurality of self-adhering labels which may be used for a variety of functions related to assisting healthcare providers in collecting a patient's blood specimen, and matching, ordering, and tracking blood products for a patient. For instance, the labels may be printed with information that may be used for tracking a patient's blood specimen from collection to testing in the laboratory, and from ordering blood products from a blood bank to ensuring that the ordered blood products are the correct products to be administered to a patient. The form may have labels and/or a wristband that assists healthcare providers in tracking the number of units of blood given to a patient. Preferably, the wristband and self-adhering labels are provided with a unique identifying bar code so that the wristband and/or form facilitates healthcare providers in providing electronic verification of blood products with a patient to minimize dangerous and wasteful misadministration of expensive blood products.

While the principal advantages and features of the present invention have been explained above, a fuller understanding of the invention in all of its various embodiments may be attained by referring to the drawings and description of the preferred embodiments below.

BRIEF DESCRIPTION OF THE DRAWINGS

FIG. 14 is a top view of a wristband/label form with the cinch slot outboard of two, full width labels contained in the tab;

FIG. 15 is a top view of a variation of the embodiment of FIG. 14 except that more full width labels are contained in the tab;

FIG. 16 is a top view of still another variation of the embodiment of FIG. 14 except that in addition to a full width label, several pairs of labels are arranged in perpendicular fashion in the tab;

FIG. 17 is a top view of yet another variation of the embodiment of FIG. 14 except that a pair of perpendicularly arranged labels are contained in the tab

FIG. 25 is a top view of a wristband form of the present invention with a wristband and labels pre-printed with common identifying indicia, and a security seal formed in the lamination layer, with FIG. 25A depicting the laminate side of the security seal with X's and surrounding colored areas; and FIG. 26 is a top view of a business form having a wristband with a bulged rectangular print area, extender, labels and security seal, with FIG. 26A depicting the laminate side of the security seal with X's and surrounding colored areas.

DETAILED DESCRIPTION OF THE PREFERRED EMBODIMENT

Figure 1:
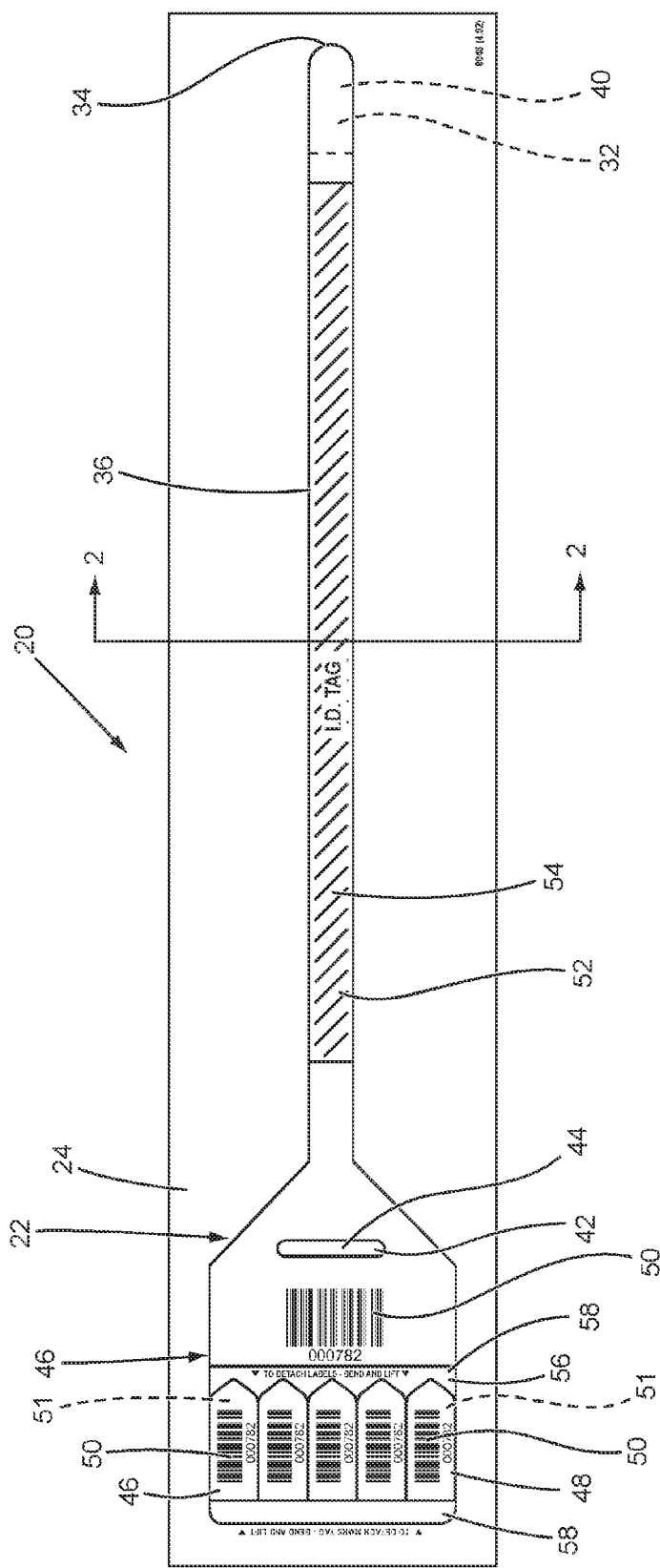
FIG. 1 depicts a top view of the first embodiment of the business form of the parent invention prior to the wristband/label assembly being separated from the carrier.
Figure 2:
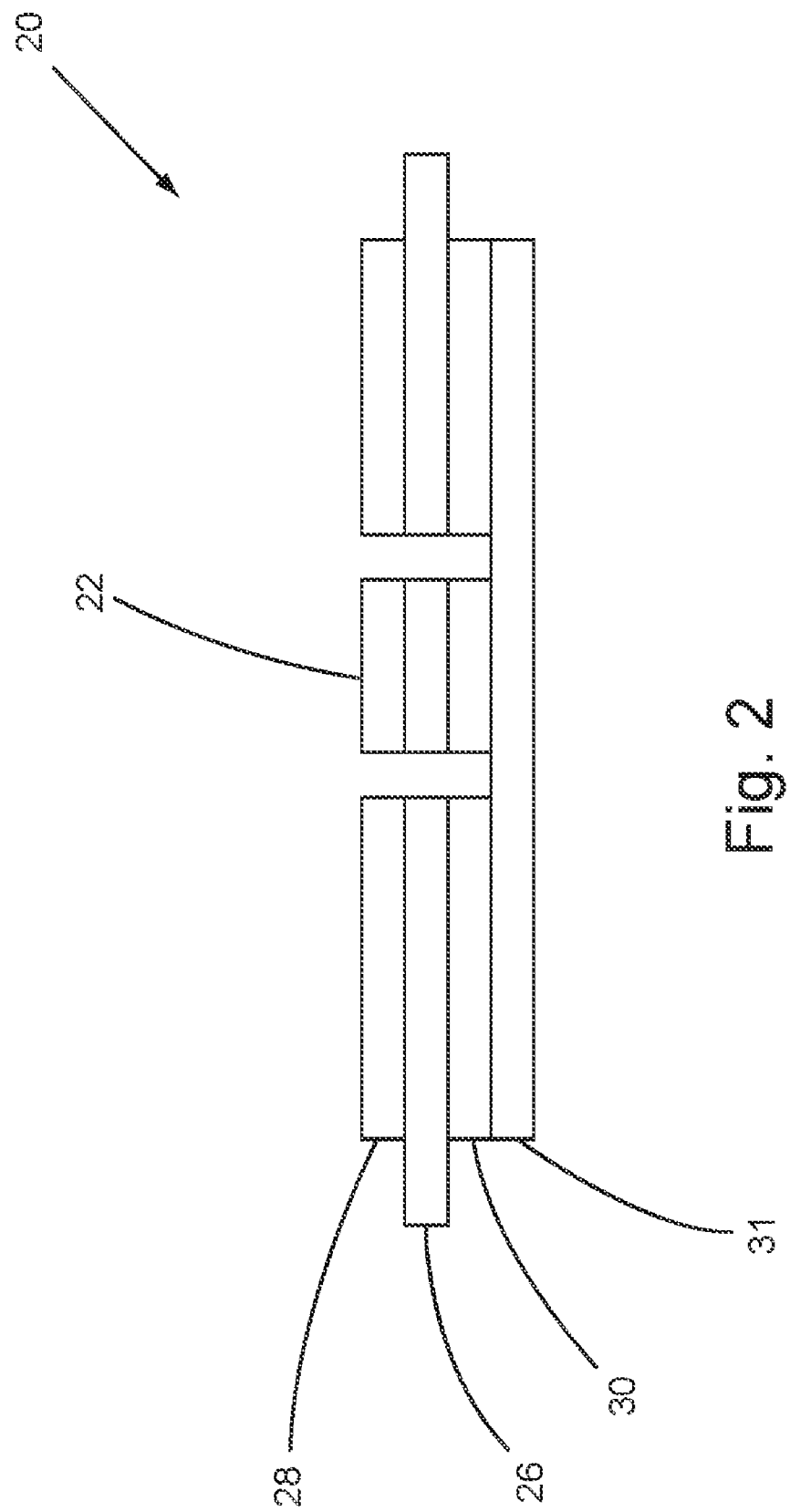
FIG. 2 is a side view of the first embodiment as shown in FIG. 1.
Figure 3:
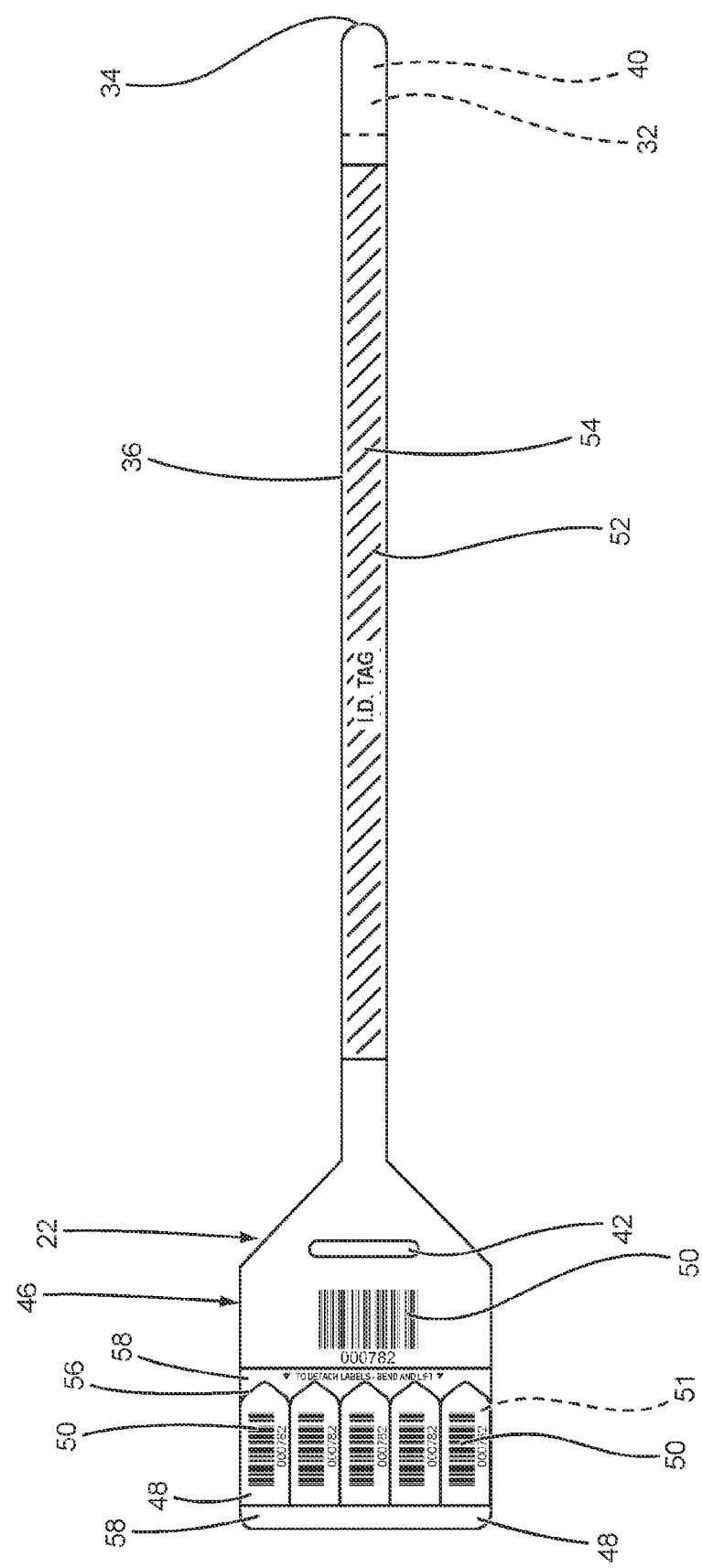
FIG. 3 is a top view of the wristband/label assembly after separation from the carrier of the first embodiment.

As shown in FIGS. 1-3, the first embodiment of the business form 20 of the parent invention generally includes a wristband/label assembly 22 die cut into a carrier 24 making an overall size of preferably approximately three and a half inches by seventeen inches, (3½"×17"). Generally, the business form 20 is assembled with a three web construction, with a poly laminated paper center web 26 sandwiched between a pair 28, 30 of thin film poly, transparent webs, and this is then dry adhered to a carrier web 31. The poly coated paper web 26 is dry adhered to the carrier web 31 so that it may be separated therefrom along its die cut to remove the wristband/label assembly 22 from the carrier 24. At an end of the form 20, an adhesive 32 is applied to the single end 34 of the wristband portion 36 of the wristband/label assembly 22. A separate patch 40, preferably made of paper with a release coating, covers the adhesive 32, with the webs die cut so that a portion of the patch 40 covering the adhesive 32 separates with the single wristband end 34 as it is separated from the carrier 24. A "cinch" comprising a slot 42 is formed when the wristband/label assembly 22 is separated from the carrier 24 as a filler 44 remains adhered to the bottom web 30.

The wristband/label assembly 22 of the first embodiment of the parent includes a wristband portion 36 and a tab portion 46. The tab portion 46 preferably includes a label portion 56 having a plurality of individual labels 48, each of which along with the body of the tab portion 46 are identified with an identifying indicia 50, preferably a bar code. While five labels 48 are shown, it is apparent to those of skill in the art that a greater or lesser number of labels could be provided in keeping with the scope of the invention. A release layer 51 preferably underlies the labels 48 and facilitates their removal from the tab portion 46 with a layer of adhesive being carried with each label for adhering the label to any other medium, such as a chart, a tag attached to a bag of belongings such as clothes, a medicine container, etc. Preferably, the wristband portion 36 also is color coded, such as with a coloring 52 along strap portion 54 of the wristband. While any convenient color scheme as known in the art may be utilized, one such convenient scheme is to use black for deceased, red for alive and needing immediate attention for survival, yellow for alive and needing attention for recovery, and green for alive and needing attention for non-life threatening injury. Other color schemes would be apparent to those of ordinary skill, and those color schemes are within the scope of the present invention. The tab portion 46 is separated from the label portion 56 by a die cut, thereby allowing for separation of the labels from the wristband portion, should that be desired, but being retained unless intentionally detached. Each of the labels 48 is defined by a die cut, and has a layer of adhesive and an underlying release layer for easy separation of each label 48 individually from the tab portion 46. Surrounding border members 58 may be peeled away from around the labels 48 to make it easier for them to be removed, such as when medical personnel have gloved hands or in the presence of fluids.

Figure 4:
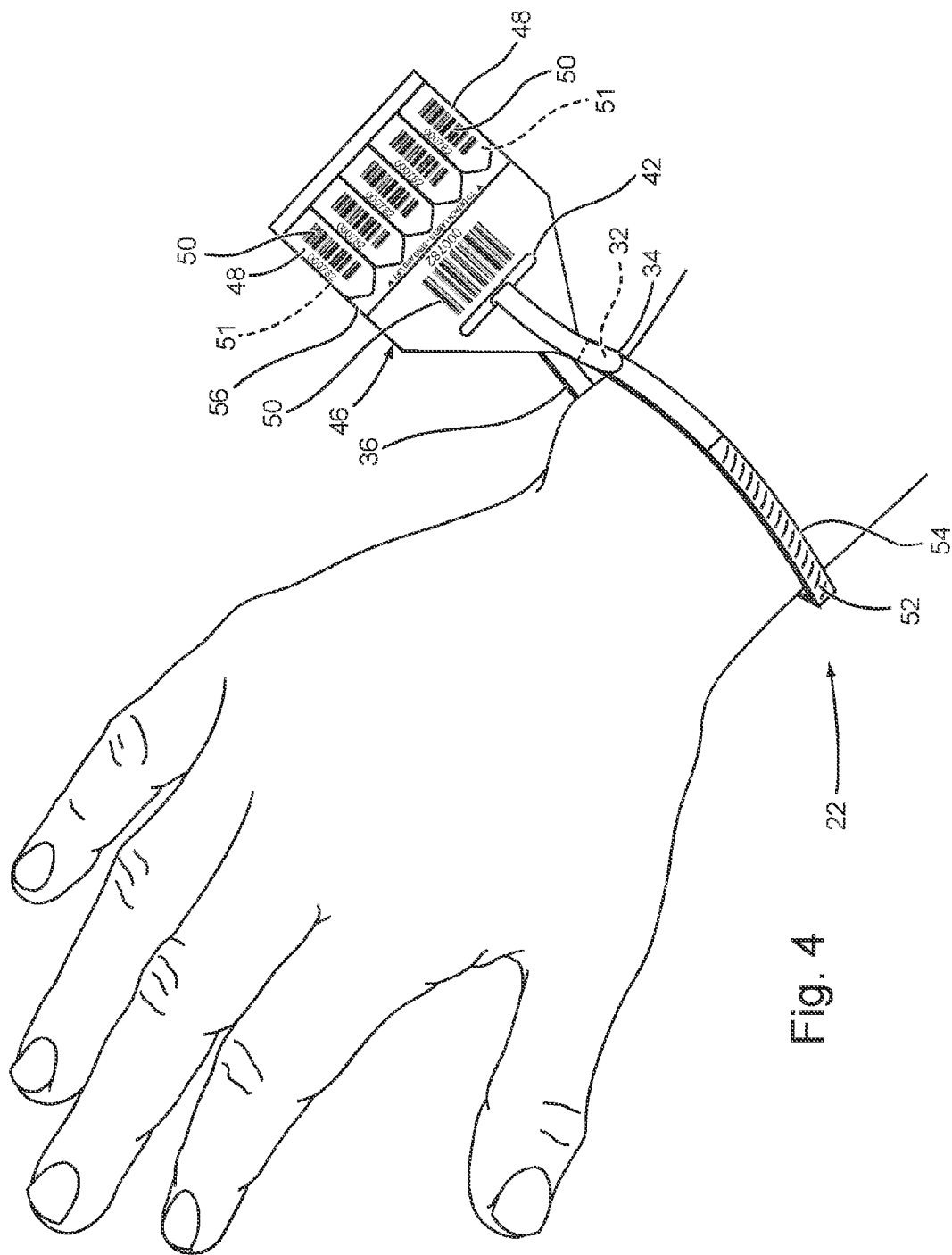
FIG. 4 is a view of the wristband/label assembly applied to a victim's appendage.

As shown in FIG. 4, the wristband/label assembly may be readily applied to a victim, such as around his wrist, by separating it from the carrier, looping the strap portion around the wrist and through the cinch or slot, pulling the strap portion tight as desired, removing the covering over the adhesive applied at the single end of the strap portion, and then affixing the single end to the strap portion to complete the circle or wristband. In this manner, a victim has been color coded as to medical condition, identified with an identifying indicia such as a bar code, and a set of labels have been made immediately available to mark any other items desired to be associated with the victim such as his possessions, his medical charts, medicines being administered, or any other item as desired.

Figure 6:
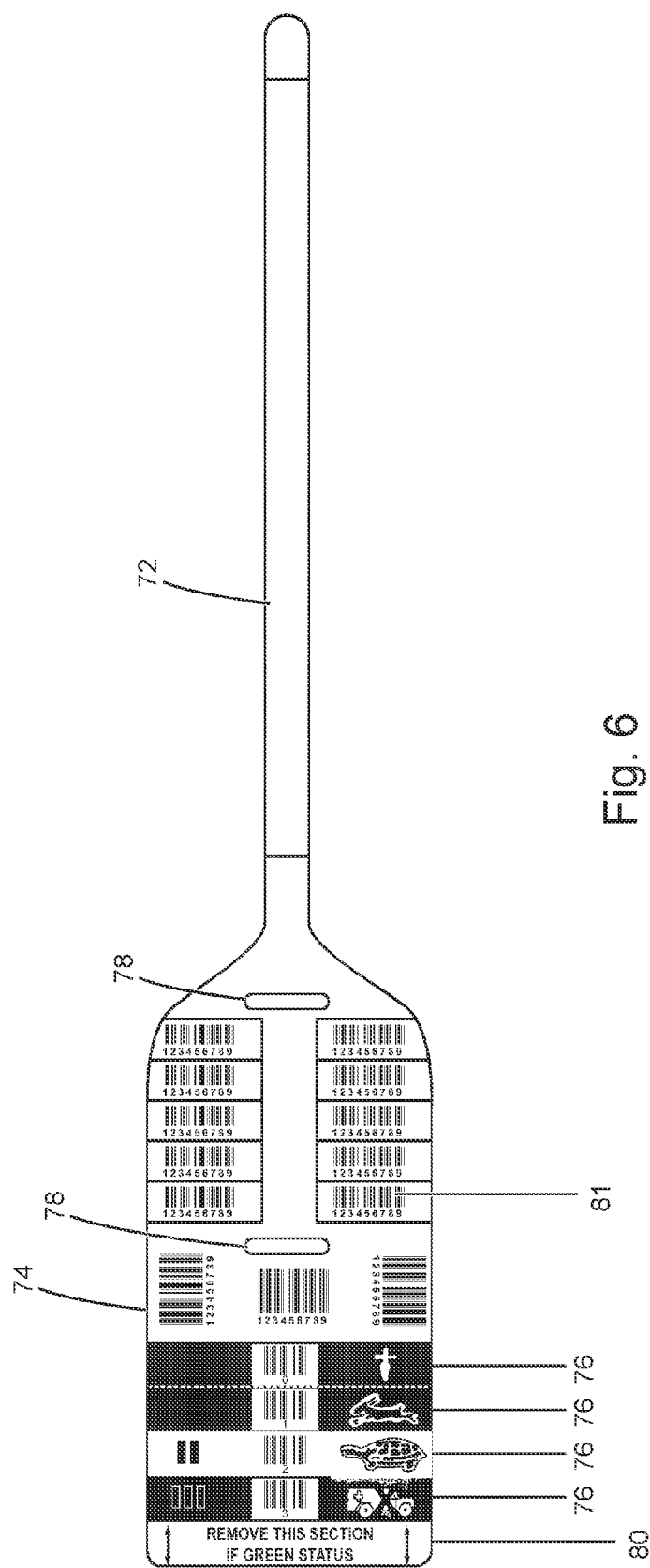
FIG. 6 is a top view of the second embodiment of the business form of the parent invention.
Figure 7:
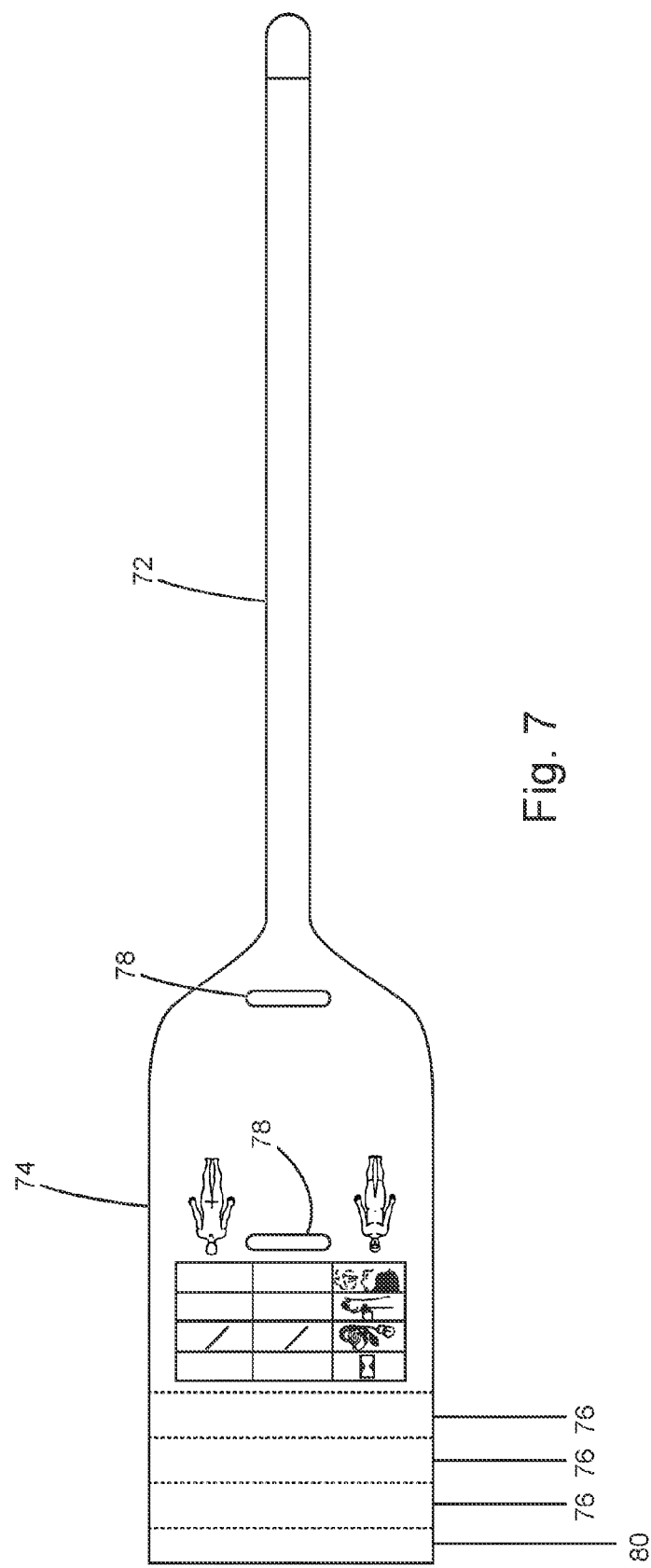
FIG. 7 is a bottom view of the second embodiment.
Figure 8:
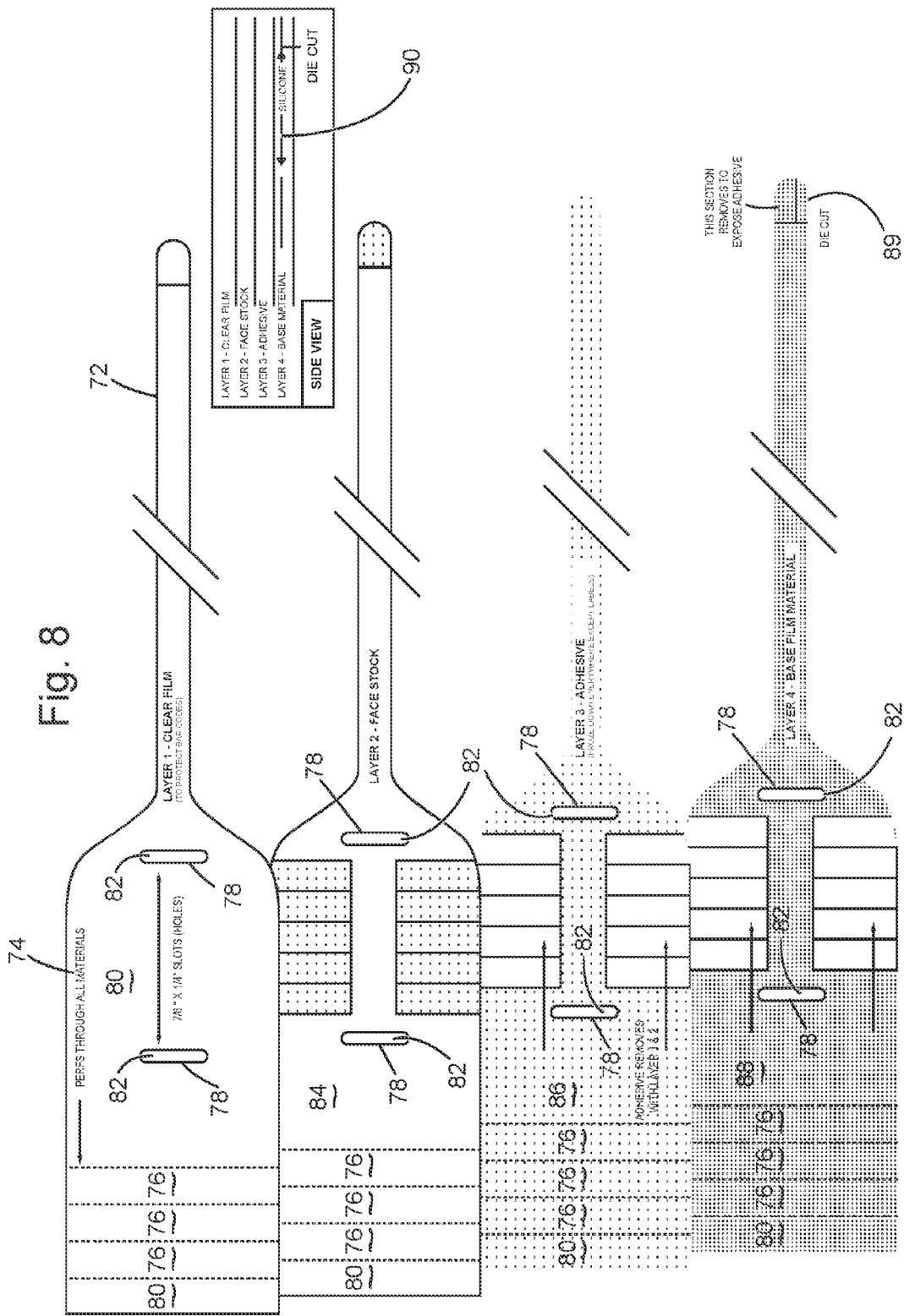
FIG. 8 is an expanded view of the second embodiment, detailing the four layers comprising the second embodiment.

The second embodiment of parent is shown in FIGS. 6-8, and is very similar to the first embodiment except that it is not supplied as part of a sheet type construction from which it must be separated prior to use, is pre-printed, has a different arrangement for indicating medical condition, etc. As shown therein, the second embodiment is completely formed and ready for use without first being separated from a carrier, as with the first embodiment. However, it also has a strap portion 72 and a tab portion 74. While the strap portion may also be color coded, it is preferred that a plurality of separable tabs 76 be provided, along with a dummy tab 80, for separation from the tab portion 74 so that an observer of the applied form may be assured that a conscious effort has been made to indicate medical condition. Otherwise, the dummy tab 80 is present indicating that this feature has not be used, at least as of yet. In addition to color coding, a bar code is also preferably indicated on the individual tabs 76 with each tab 76 having a matching bar code so that the victim's condition may be also scanned into the computer or data base at the same time as the patient's ID bar code. Further information may also be provided on the tabs 76, such as definitional information to instruct a medical technician as to the specific meaning to the various categories to help ensure consistency in marking victims despite the use of multiple and even untrained personnel. This information helps to make the present form almost self teaching as one never knows the quality or training of personnel who will be available when a medical emergency occurs. As shown in FIG. 7, the back of the tab portion 74 may also have additional instructing information, or a place for recordal of vital signs or other medical information such as allergies to medicine or the like. Of further note, as shown in this second embodiment is not one but two cinches 78, comprising slots. This allows the strap portion 72 to be sized more closely to varying dimensions and thus used with a wider variety of appendages. Other similar features are also included such as the bar code labels 81, shown arranged in two columns between the cinch slots 78.

FIG. 8 depicts the four layers used to form the second embodiment, as preferred. The top layer is a web 80 of a clear protective film extending across the entirety of the form, and perforated as noted to allow for the tearing off of tabs 76, 80, and with holes 82 forming the cinch 78. The second layer is comprised of a face stock 84, preferably pre-printed with information as desired with the majority of information contained in the form. The next layer is an adhesive layer 86, preferably a patterned layer and release coating as known in the art as shown, which allows for the removal of tabs 86 with a layer of self adhesive for applying the bar code on ancillary items, as explained in greater detail below. The bottom layer is a web 88 of a base film material which acts to protect the bottom of the face stock web 80. As is noted in the Figures, a patch 89 similar to patch 40 of the first embodiment is shown and which is used to attach the end of strap portion 72 and complete the wristband about the victim's appendage. More particularly, two sections of silicone 90 are shown in a side view inset in FIG. 8, with those sections of silicone lining up with the patch 89 and the bar code labels 81 so that upon separation they carry with them the layer of adhesive making them self adhering.

Figure 5:
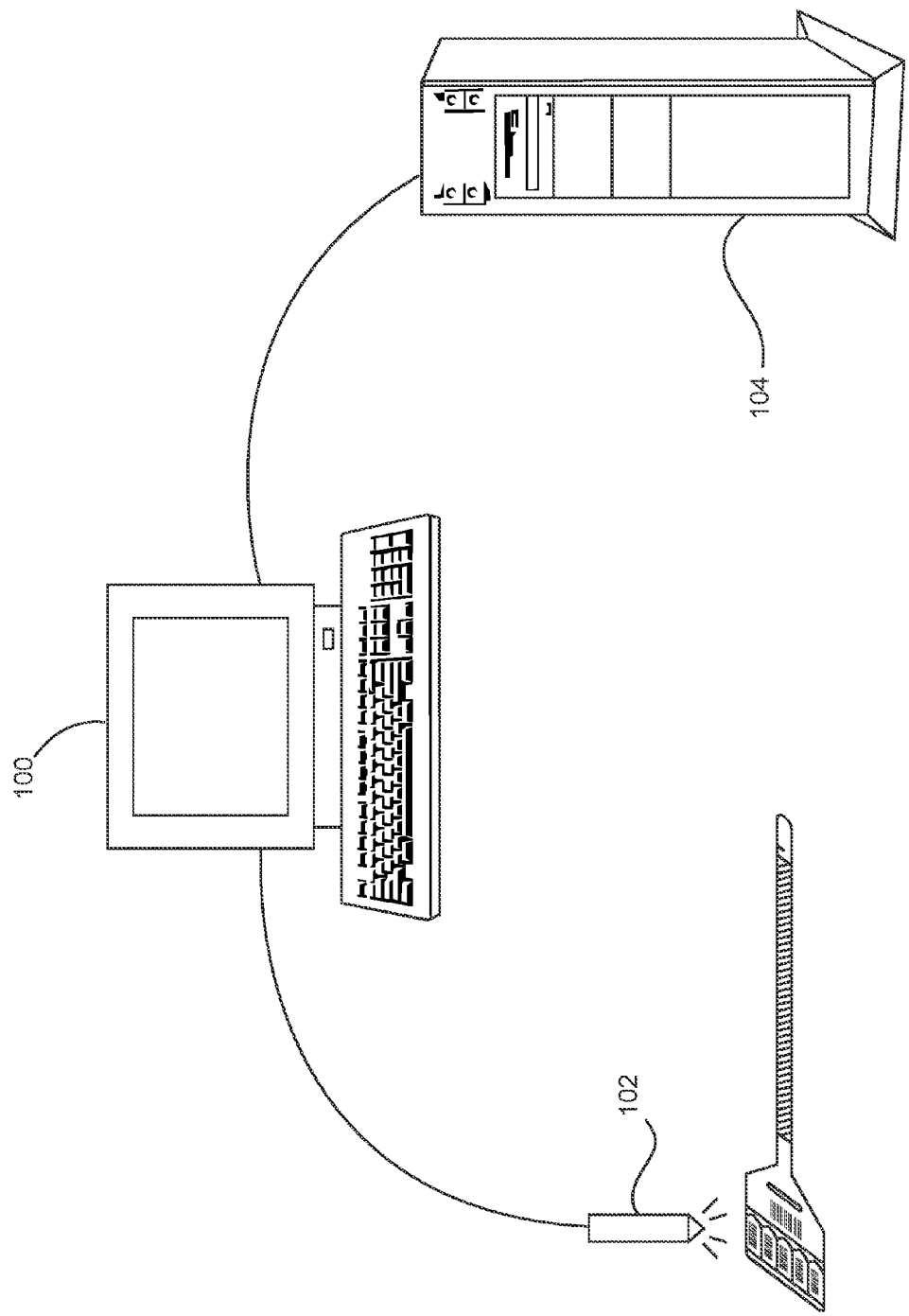
FIG. 5 is a diagram of the computer system used to implement the method of collecting and displaying over the interne the victim data.

As shown in FIG. 5, as the victims are processed, the parent invention also contemplates that this information may be input to a computer 100, the bar code being read in with a bar code swiper 102 or the like for preferably both of patient ID and medical condition, and then this information may be transmitted over the internet to a server 104 for collating and display at a web site. Multiple computers 102 could be readily connected to the same server 104, as is known in the art, and handle the input from a number of medical facilities at the same time. This permits this information to be made available almost immediately as victims are processed, through the web and at remote locations, eliminating the anxiety of family members who physically search for their relatives or loved ones.

While the principal advantages and features of the parent invention have been illustrated through an explanation of its preferred embodiment, there are other aspects and variations of the parent invention as would be apparent to those of skill in the art. For example, rather than bar coding, other identifying indicia could be used on the form. The form could be used in other applications other than in emergency situations in the field. Rather than color coding, other coding or indicators could be used to sort victims, or they could be sorted into other categories according to differing medical categories, or coding could be dropped from the form, as desired. Other construction could be used for the form, including especially the wristband portion, such as self laminating construction and the wristband would still be protected from damage during its single use. Other means could be used to attach the wristband rather than looping a single end around and through a slot. Another form of a cinch could be used, or a different arrangement of the cinch. Still other variations would be apparent to those of skill in the art, and the parent invention is intended to be limited solely by the scope of the claims appended hereto, and their legal equivalents.

Figure 9:
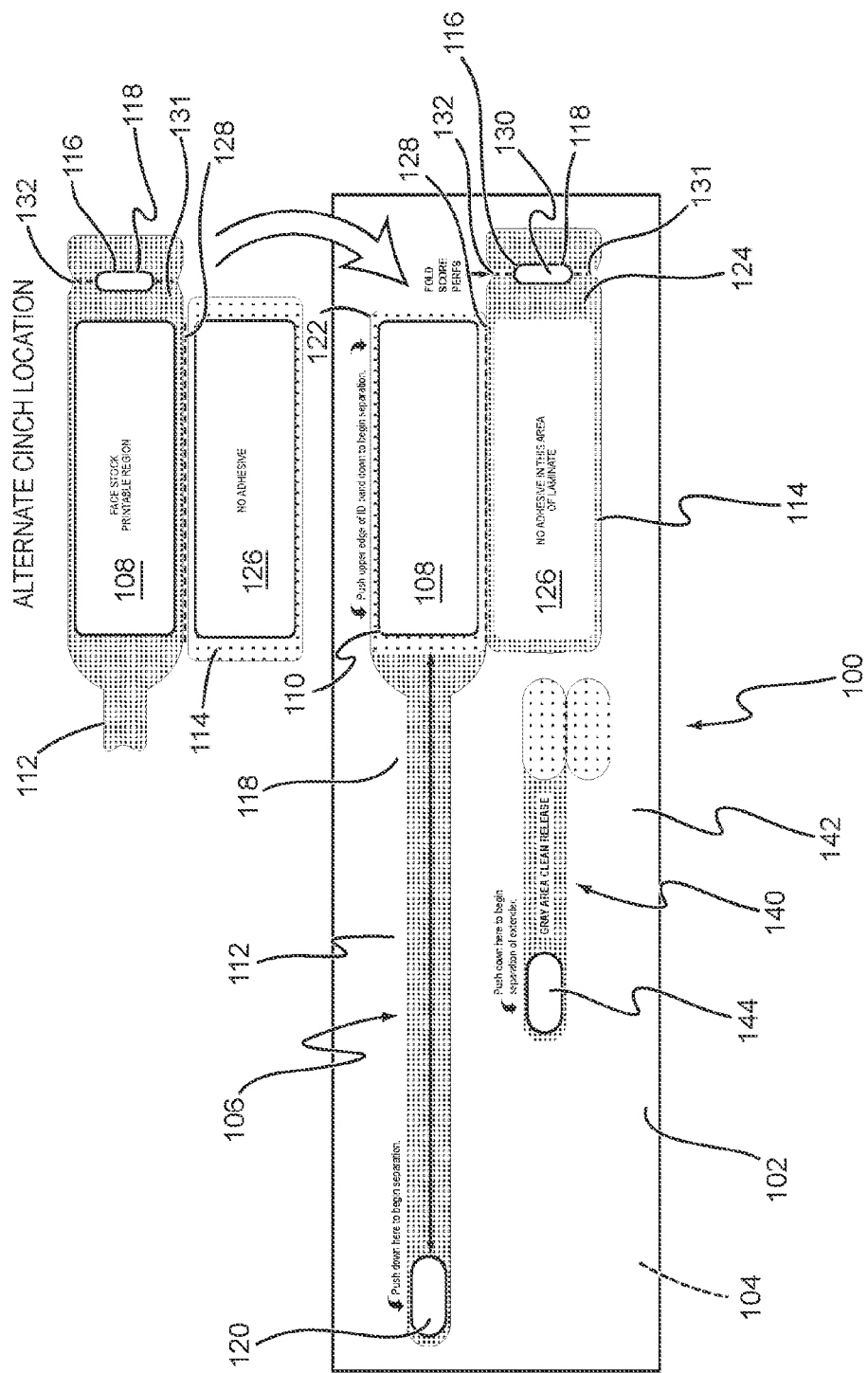
FIG. 9 is a top view of the first embodiment of the self laminating wristband with an inset depicting an alternate location for the cinch, and an extender formed in an approximately envelope size sheetlet.

The invention 100 of the second parent invention is shown in FIG. 9 and is depicted therein as formed in a two layer, sheetlet sized construction of about 3 inches by 11 inches. The top layer 102 is preferably a face stock, such as bond or the like as would readily accept a printed image from a laser printer or other computer controlled printer, and a bottom laminate layer 104 which underlies the face stock layer 102 and is joined by a patterned adhesive layer including portions which are release coated, as will become apparent upon further reading. The invention 100 generally comprises a self laminating wristband 106 having a printable region 108 of face stock defined by a die cut 110 therein, and an integrally formed strap portion 112, laminating portion 114, and cinch 116 similarly formed by a die cut 118 in the laminate layer 104. A patch of face stock 120 is also die cut into the face stock layer 102, and covers a patch of adhesive with which the strap portion is adhered as the wristband 106 is applied to a patient, as will be explained. The length of strap portion 112 is covered by a release coating so that after it is removed from the sheetlet 100 it does not carry any adhesive with it. The laminating portion 114 has a layer of adhesive between a top portion thereof 122 and the face stock region 108 to adhere it thereto. However, a bottom portion 124 of the laminating portion 114 has a window 126 of area where no adhesive is applied so that as the laminating portion is folded over there is no layer of adhesive covering the printable region 108. A fold or perf line 128 if formed between the laminating portion halves 122, 124 as an aid in forming the wristband 106 after it is separated from the sheetlet 100. The cinch 116 generally comprises a slot 130 formed in an extension 131 and aligned generally perpendicularly to the face stock region 108 and strap portion 112 for easy insertion of the strap portion 112 therethrough. There is also provided a fold or perf line 132 along the central axis of the slot 130 through the width of the extension 131, and adhesive covers the extension 131 so that the extension 131 may be folded over onto the strap portion 112 after it has been threaded through the slot 130 to its desired length. The extension 131 and cinch 116 are shown to be adjacent the bottom half 124 of laminating portion 114, which results in the adhesive layer of the extension 131 facing towards the patient's wrist as the wristband is applied. Alternatively, the extension 131 and cinch 116 may be formed adjacent the top half 122 of the laminating portion 114 as shown in the inset of FIG. 9 and with this construction the extension adhesive faces away from the patient as the wristband is applied. With this alternative arrangement, the wristband may lie flatter against the patient, as the other arrangement creates a small tab which may or may not lie flat depending on how tight the wristband is drawn. However, this is not considered significant.

In use, this wristband embodiment is first separated from the carrier sheetlet by pushing down on the end of the strap and/or the die cut face stock area 108, and peeling it away, thereby separating a matrix comprising the wristband assembly. The laminating portion 114 is then folded together to enclose the printed face stock region. The wristband is next applied to the patient's wrist by wrapping the strap about the wrist, inserting it through the cinch, folding over the extension to adhere it to the strap, and then exposing the adhesive on the end of the strap and adhering it back onto itself to secure the excess strap. The caregiver can choose the tightness of the wristband by threading more or less of the strap through the slot in the cinch before adhering the strap to the extension.

Also shown on the sheetlet 100 is an extender 140 generally comprising a clamshell joinder portion 142 at one end of a length of laminate layer 104 and a patch of face stock 144 covering a patch of adhesive at the other end. The extender 140 may be used to extend the effective length of strap portion 112 and is applied by adhering the clamshell portion 142 anywhere along the length of strap portion 112 and using the patch of adhesive on the extender 140 to join the strap portion 112 to itself as just described. The length of extender 140 is adhesive free, as the strap portion 112, so that no adhesive is exposed to the patient's skin.

Figure 10:
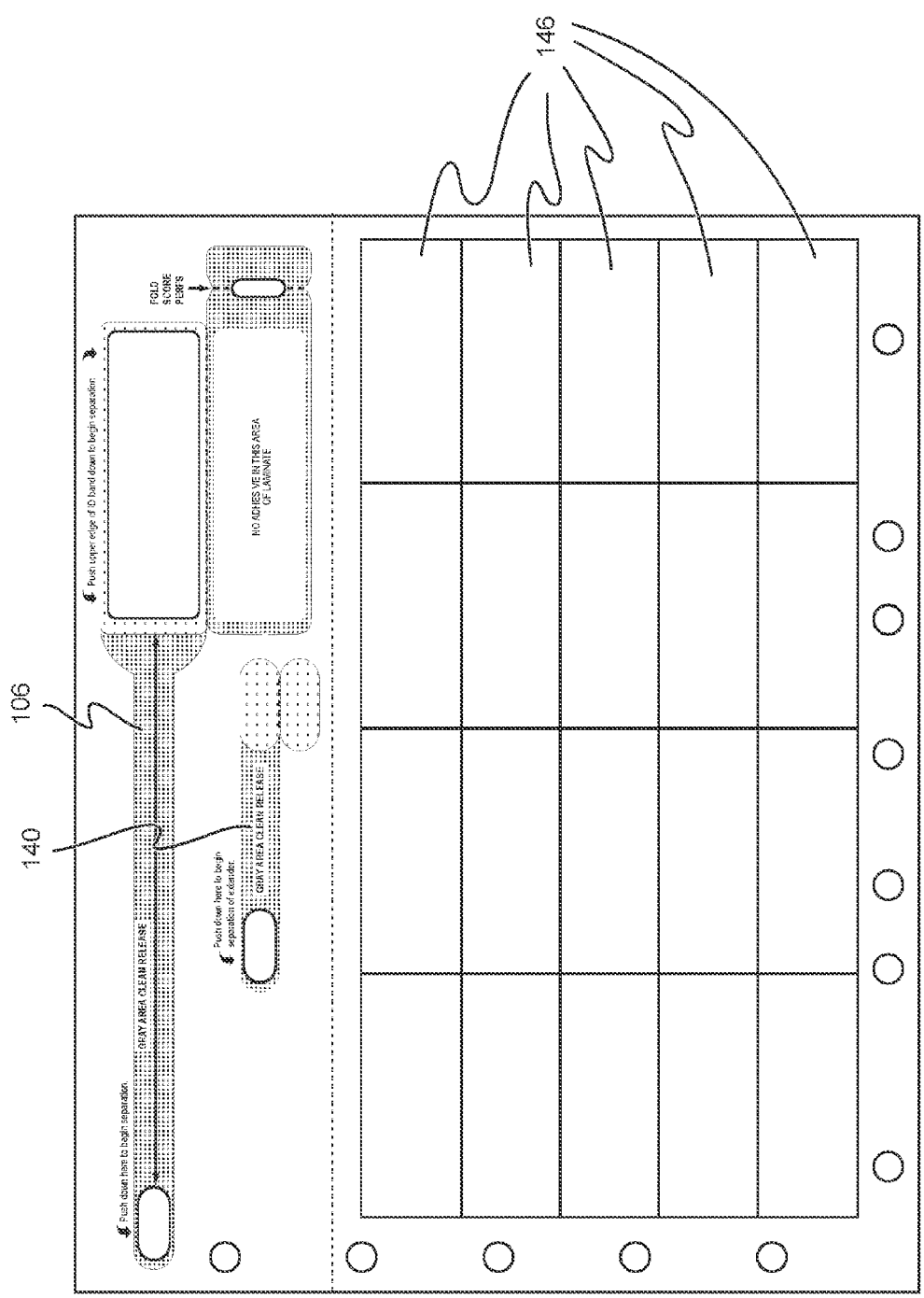
FIG. 10 is a top view of the first embodiment of the self laminating wristband and extender formed in a page sized sheet with a plurality of self adhering labels.

As shown in FIG. 10, the wristband 106 and extender 140 may be included as part of a page sized sheet along with a plurality of self adhered labels 146. As with previous inventions shown in the inventor's prior patents, it has been found to be desirable to print identifying information relating to a patient not only on a wristband but also on labels which may then be separately peeled off as needed to label items dedicated for use by the patient or to identify other medical items such as blood samples, tissue samples, etc. Thus there has found to be a need for the present invention configured as shown in FIG. 10.

Figure 11:
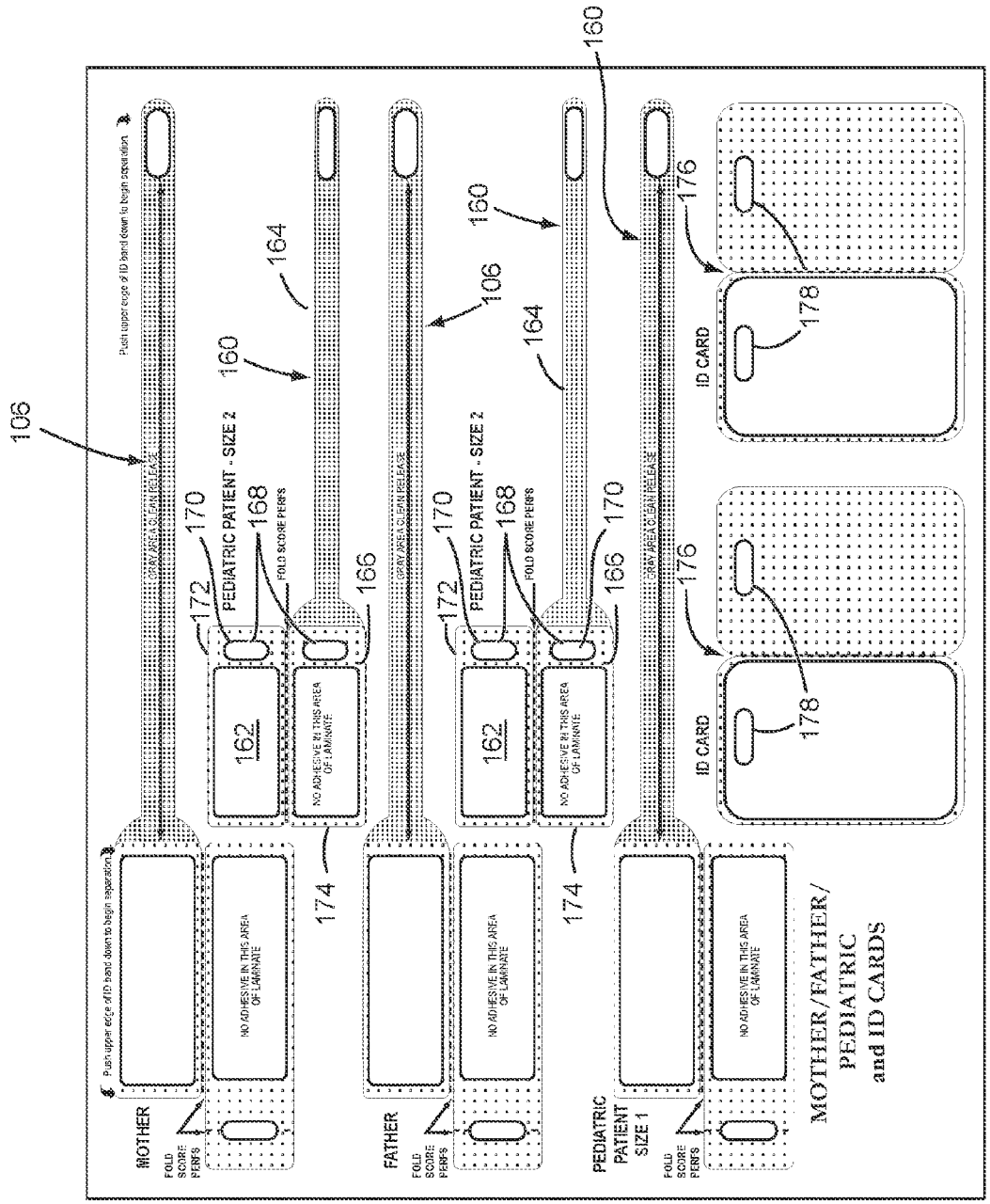
FIG. 11 is a top view of a page sized sheet having a plurality of self laminating wristbands of varying lengths, and depicting an alternate construction for the wristband, coupled with a pair of ID cards.

As shown in FIG. 11, a page sized form may also be provided with a mix of wristbands 106 as well as a different embodiment of wristband 160, which is preferably somewhat smaller in length than wristband 106, and which has a slightly different arrangement for the cinch. As shown therein, there are two wristbands 160, each of which has a printable face stock region 162 die cut from the face stock layer as with wristband 106. And, a strap portion 164, laminating portion 166 and cinch portion 168 are also die cut into the laminate layer, as with wristband 106. However, cinch portion 168 comprises a pair of slots 170 die cut adjacent both of the top half 172 and bottom half 174 of laminating portion 166, so that as the two halves 172, 174 are folded over to laminate faces stock region 162, the slots 170 are aligned to overlie each other and create a single opening intermediate the face stock region 162 and strap portion 164. With the cinch located in this position, several differences are noticeable. First, the wristband 160 may conveniently circumscribe a smaller circumference so that it may readily fit onto a smaller wrist, such as a baby's, as it takes the face stock region 162 and laminating portion 166 out of the loop forming the wristband. Instead, the face stock region 162 and laminating portion 166 form into a "hang tag" which essentially hangs from the strap portion 164 after the wristband 160 is applied to a patient. Note that the strap portion 164 extends from the bottom half 174 in this embodiment instead of from the top half 172 as in the first embodiment, thereby allowing the strap portion 164 to wrap around and through the cinch portion 168 and then back onto itself without passing over or obscuring the face stock region 162. Although this wristband 160 construction is shown as being adapted for smaller wrists, it may also be used with a longer strap portion 164, or with an extender 140, and may be viewed as a matter of design choice. Also shown on the sheet are a pair of ID cards 176, that are themselves self laminating, with a slot 178 for convenient attachment directly to either of the wristbands 106, 160, or separately to a clip or for being carried in a user's wallet. This assemblage of wristbands and ID cards has been found to be especially useful for pediatric situations with a wristband for each parent, an ID card for each parent, and two smaller wristbands for one or two babies or children.

Figure 12:
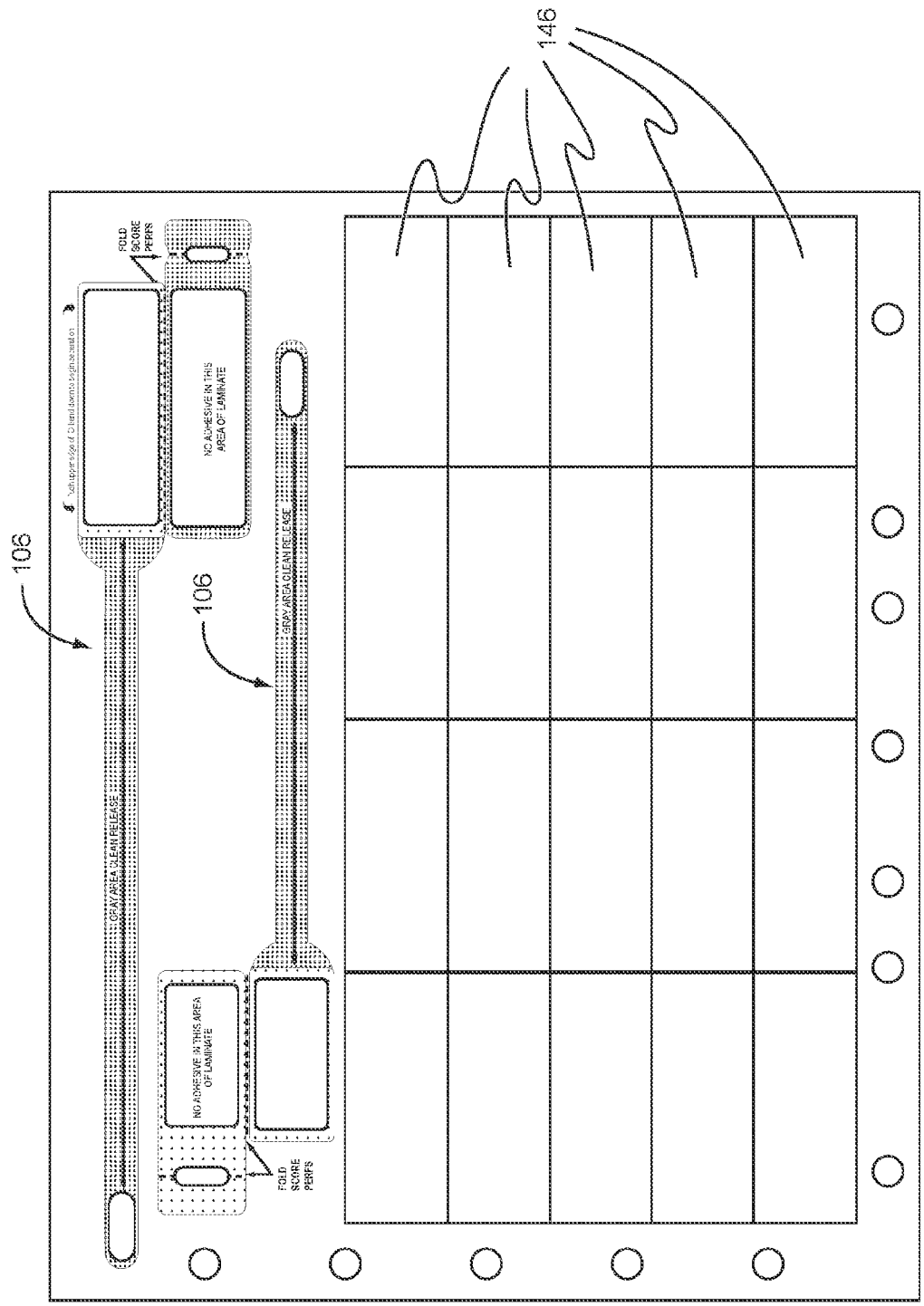
FIG. 12 is a top view of a page sized sheet having a pair of wristbands and a plurality of self adhering labels.

FIG. 12 depicts a sheet sized form containing two wristbands 106 along with a plurality of self adhering labels 146 which is a slightly different configuration than that shown in FIG. 10, but with the same inventive wristbands being used.

Figure 13:
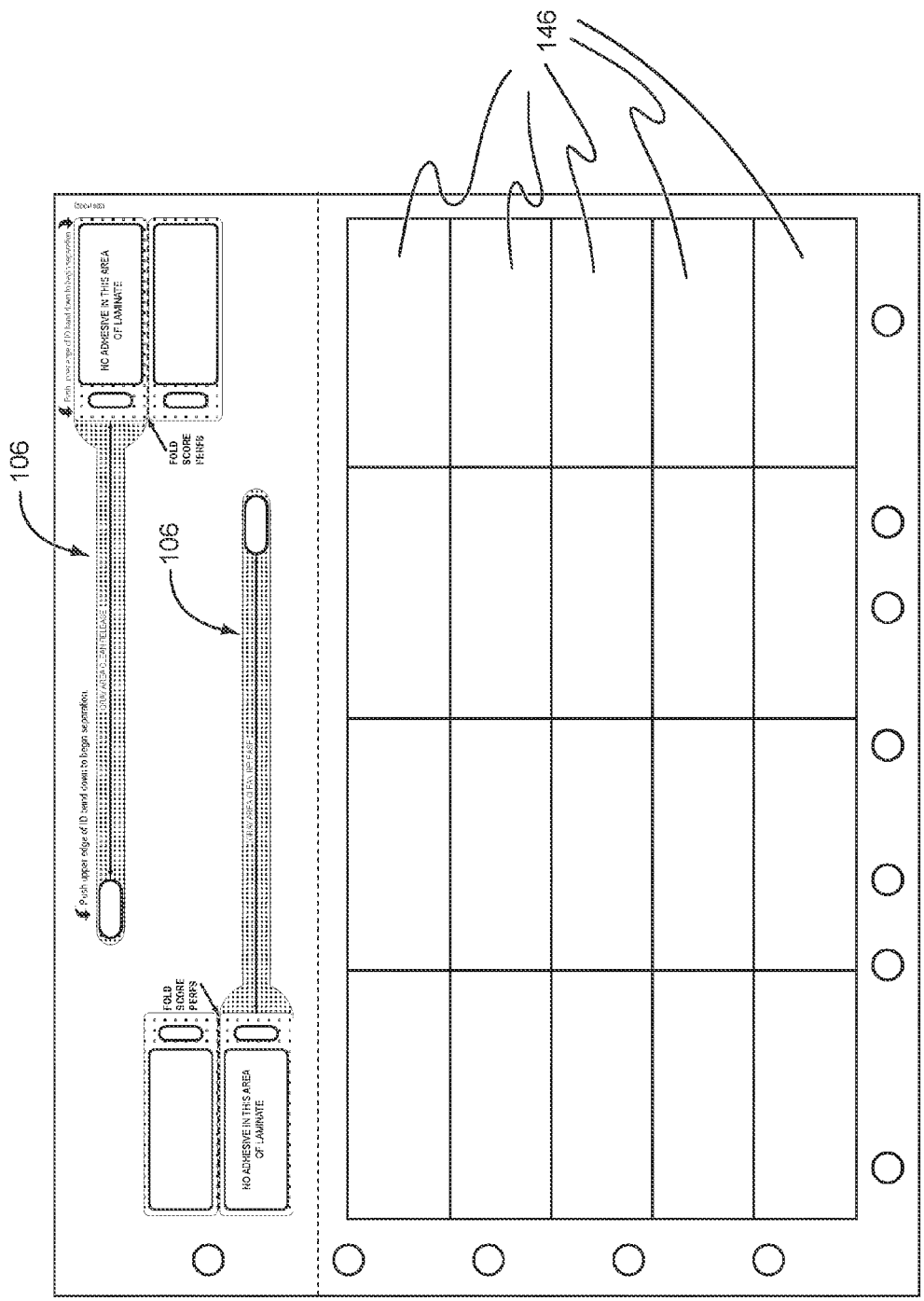
FIG. 13 is a top view of a page sized sheet having a pair of wristbands of alternate construction and a plurality of self adhering labels.

FIG. 13 depicts a sheet sized form similar to that shown in FIG. 12 except that an alternative wristband 160 is used. While the inventor has found that these particular groupings of products have met with acceptance and commercial success for particular applications, other combinations of wristbands, of different construction, with or without labels or ID cards, may be found desirable as a matter of design choice.

FIG. 14 depicts an embodiment of the invention disclosed in the parent application. As shown therein, a wristband 200 has a strap portion 202 and a tab 204 which contains a cinch slot 206 and a pair of full width labels 208. Each of the labels 208 and the adjacent area of the strap portion 202 are encoded with identifying indicia 210, shown as preferably bar coding. An imprint area 212 is included on the strap portion 202 which may be imprinted with any desired identifier such as the company or hospital name, or other message or the like. The construction of this invention may be similar to that described above, with a multi-web arrangement as described for the embodiment of FIG. 1. The labels may be removed and applied to any other associated materials, depending on the use made of the wristband. In a medical setting, the labels may be used for medical charts, medicines, eating utensils, clothing bags, or any other commonly known need. In other applications, other uses may be made, such as for personal items, tickets, receipts, charge identifiers such as for a credit card charge, etc., as limited only by the imagination of the user.

The embodiment shown in FIG. 14 has a generally slender strap portion 202 which may be more comfortable for a person to wear about his wrist, and the cinch slot 206 may be slightly wider than the width of the strap portion 202 to facilitate its insertion as the wristband 200 is secured. A protective patch 214 of may conveniently cover a patch 216 of adhesive at the tip of the strap portion 202 until it is desired to apply the wristband 200 to a person. After insertion through the cinch slot 206, the patch 214 may be removed and the strap portion 202 folded over and adhered onto itself to complete the application process. The strap portion 202 may be tightened about the person by pulling on it after it has been inserted so as to achieve a tight banding of the wristband about the person's appendage. Alternately, the strap portion 202 need not be tightened, and the wristband 200 left "loose" to provide a secure but perhaps more comfortable fit.

Label variations of the basic arrangement shown in FIG. 14 are depicted in FIGS. 15-17. These include a plurality (5) of labels 208 all arranged in the same full width orientation as shown in FIG. 15, a single full width label and two pairs of perpendicularly arranged labels as shown in FIG. 16, and a single pair of perpendicularly arranged labels as shown in FIG. 17. While these label arrangements are shown as anticipated to most desirably meet the needs of intended users, it would be apparent to those of skill in the art that other label arrangements could be used without departing from the scope of the invention.

Figure 18:
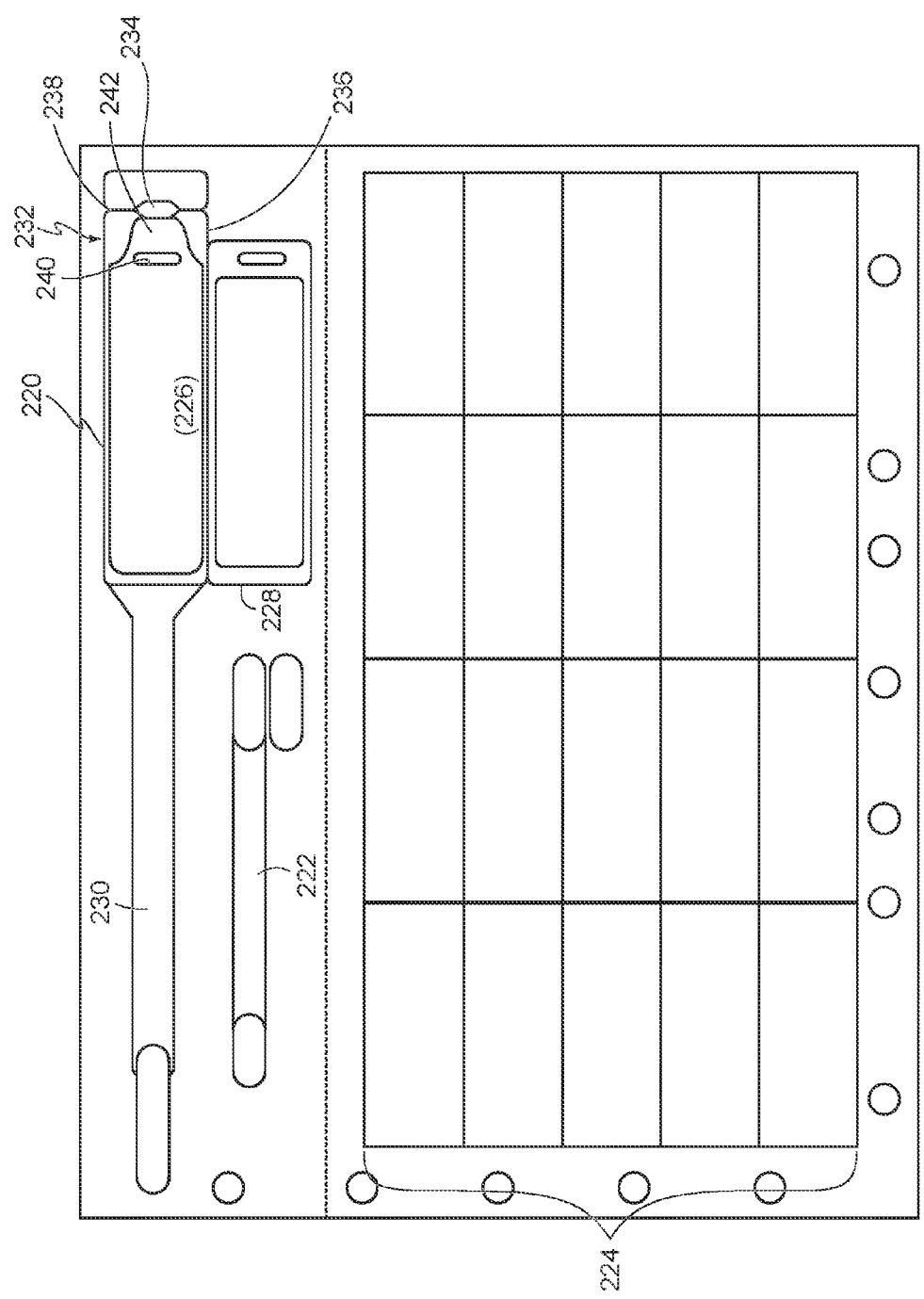
FIG. 18 is a top view of a page sized sheet having a wristband with outboard cinch slots, an extender and a matrix of labels.

Depicted in FIG. 18 is an approximately page sized sheet containing a self laminating wristband 220, an extender 222 and a plurality of self adhering labels 224. The various webs used in constructing this sheet have been explained above. The self laminating wristband 220 includes a face ply portion 226 preferably formed in the face stock layer, a lamination layer portion 228 preferably formed in the lamination layer, a strap portion 230 also preferably formed in the lamination layer, and an attachment portion 232 preferably formed in the lamination layer. As shown in FIG. 18, one slot 234 is formed in an extension part 236 of the attachment portion 232. A fold line 238 bisects the slot 234 as an aid in folding the slot 234 over to adhere the strap portion 230 as will be explained. As shown, the fold line 238 may comprise an incomplete cut at either side, through the central axis of the slot 234 and through the lamination layer. A layer of adhesive substantially surrounds slot 234 so that as it is folded over it adheres to the strap portion inserted therethrough. A second slot 240 may be formed in both of the face ply or stock portion 226 and in the underlying lamination layer. The face stock portion 226 has a tab 242 extending from the edge of the generally rectangularly shaped print or image area and up to the edge of the slot 234.

In use, the sheet may be first processed through a laser printer or the like to apply information to the labels 224 and the wristband 220, such as a patient's name, hospital admission number, or other information. The wristband may then be separated from the sheet and applied to a patient's wrist much as described above in connection with the other embodiments of the parent invention except that the strap end is inserted through slot 234 and then the tab is folded over to adhere the strap end in place. Adhesive need not be applied to the end of the strap as in other embodiments and instead the adhesive applied to the area substantially surrounding the tab slot secures the strap in place. It is noted that the face stock tab 242 shields the strap end from contacting a surface with adhesive and that unlike other embodiments there is no adhesive on the strap end which moves past the patient's wrist as the wristband is applied. This helps to ensure that the wristband doesn't become "fouled" as it is applied, making the wristband even more likely to be applied successfully to difficult or uncooperative patients. The extender 222 may be used as described with other embodiments to extend the effective length of the wristband 220, and the extender similarly need not have adhesive applied to its end.

Figure 19:
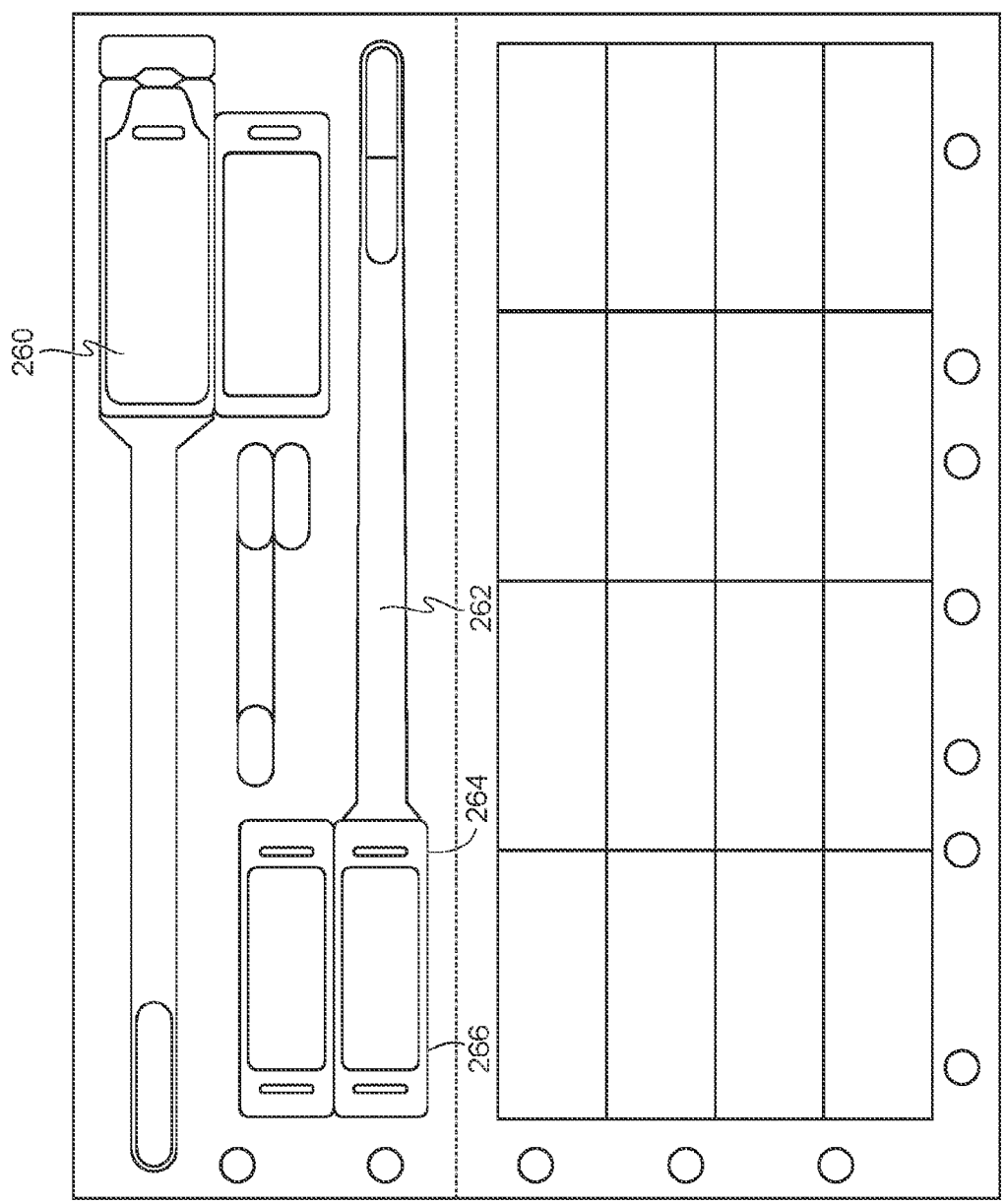
FIG. 19 is a top view of a page sized sheet having a pair of wristbands with one wristband having a pair of outboard cinch slots, another wristband having a cinch slot on either side of the face stock, an extender for use with either, and a matrix of labels.

FIG. 19 depicts another arrangement of wristbands and labels similar to that of FIG. 18 except that two wristbands are provided, of generally shorter length, and with a different slot arrangement for one of the wristbands. The wristband 260 shown near the top of the sheet is designed the same as the wristband 220 as shown in FIG. 18. As explained above, this wristband 260 is conveniently applied about a patient's wrist. The second wristband 262 has a cinch slot 264, 266 on either side of the face stock portion 268, and the strap end 270 has a patch of adhesive 272. In use the second wristband may be applied in several different orientations. One such orientation is for the strap end to be inserted through both slots 264, 266, passing underneath the face stock portion 268. In this orientation the face stock portion has a tendency to stay flatter after the wristband is applied and, with infants or small wrists or other tightly drawn wristbands, this flatter orientation aids in reading any bar coded information on the face stock. Another orientation is for the strap end to be inserted through the inboard cinch slot 264 so that the face stock portion 268 hangs freely from the wristband 260. Still another orientation is for the strap end to be inserted through the outboard cinch slot 266 which is very similar to that as described above for other embodiments. In this orientation, the wristband is at maximum length with the face stock portion 268 forming part of the wristband circle, and the strap end folded back onto itself for attachment. These two wristbands form a unique combination for application to pediatric cases as the different wristband constructions allow for wristbands to be applied to both arms and legs of infants, in different orientations, all with only one sheet being consumed.

Figure 20:
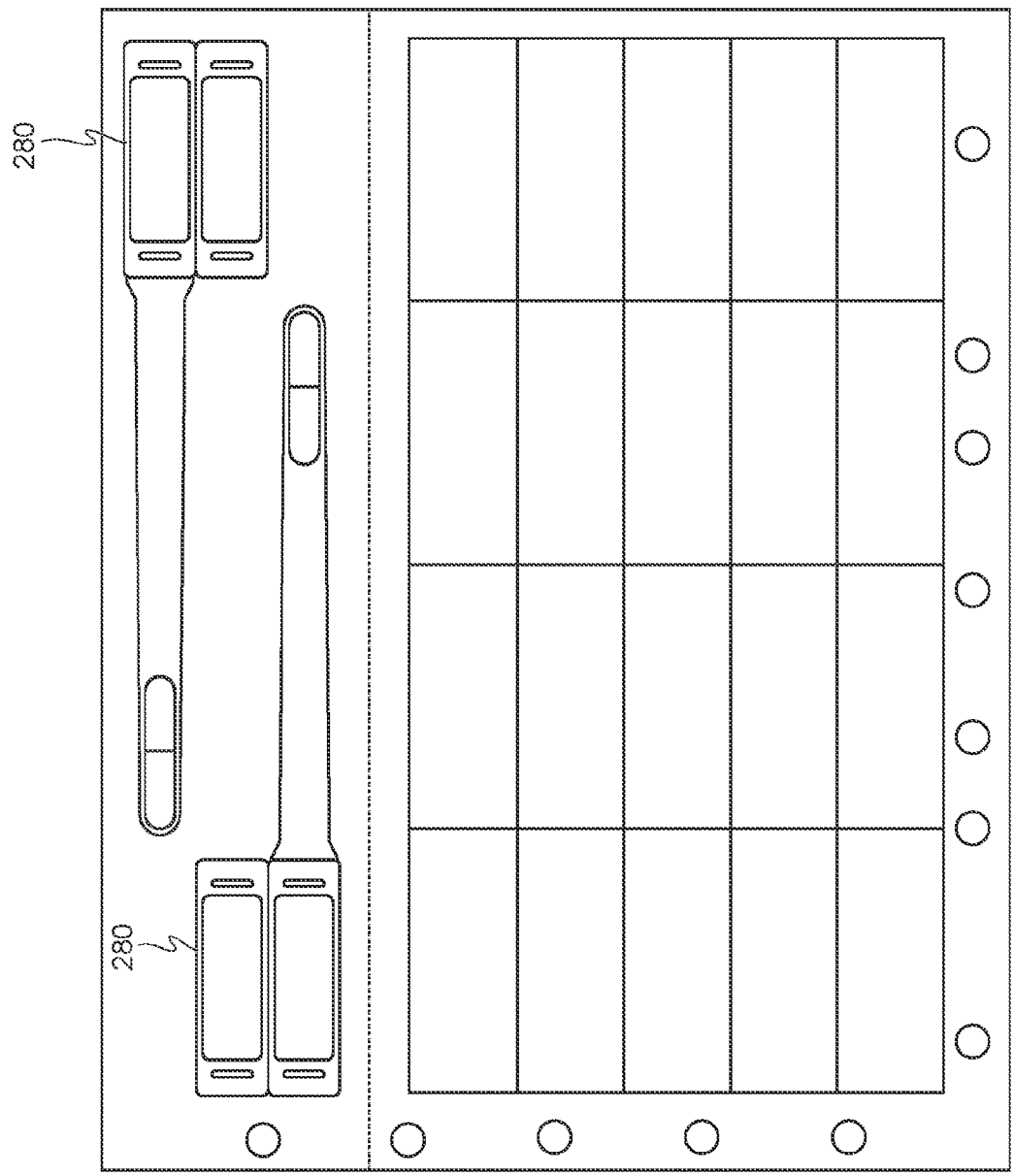
FIG. 20 is a top view of a page sized sheet having a pair of wristbands each having a cinch slot on either side of the face stock.

The sheet depicted in FIG. 20 provides two wristbands 280 along with a plurality of self adhering labels 282. In this embodiment the two wristbands 280 are of the same design as the wristband 262 as shown in FIG. 19. This arrangement is particularly adapted for use with neo-natal intensive care unit infants, as the two wristbands may both be arranged in either of two orientations, as explained above, which allows for maximum flexibility in applying two wristbands to either arms or legs of infants undergoing intensive care. In this situation, many different kinds of conditions are encountered and this flexibility allows for their successful use with consumption of a single wristband form and label set.

Figure 21:
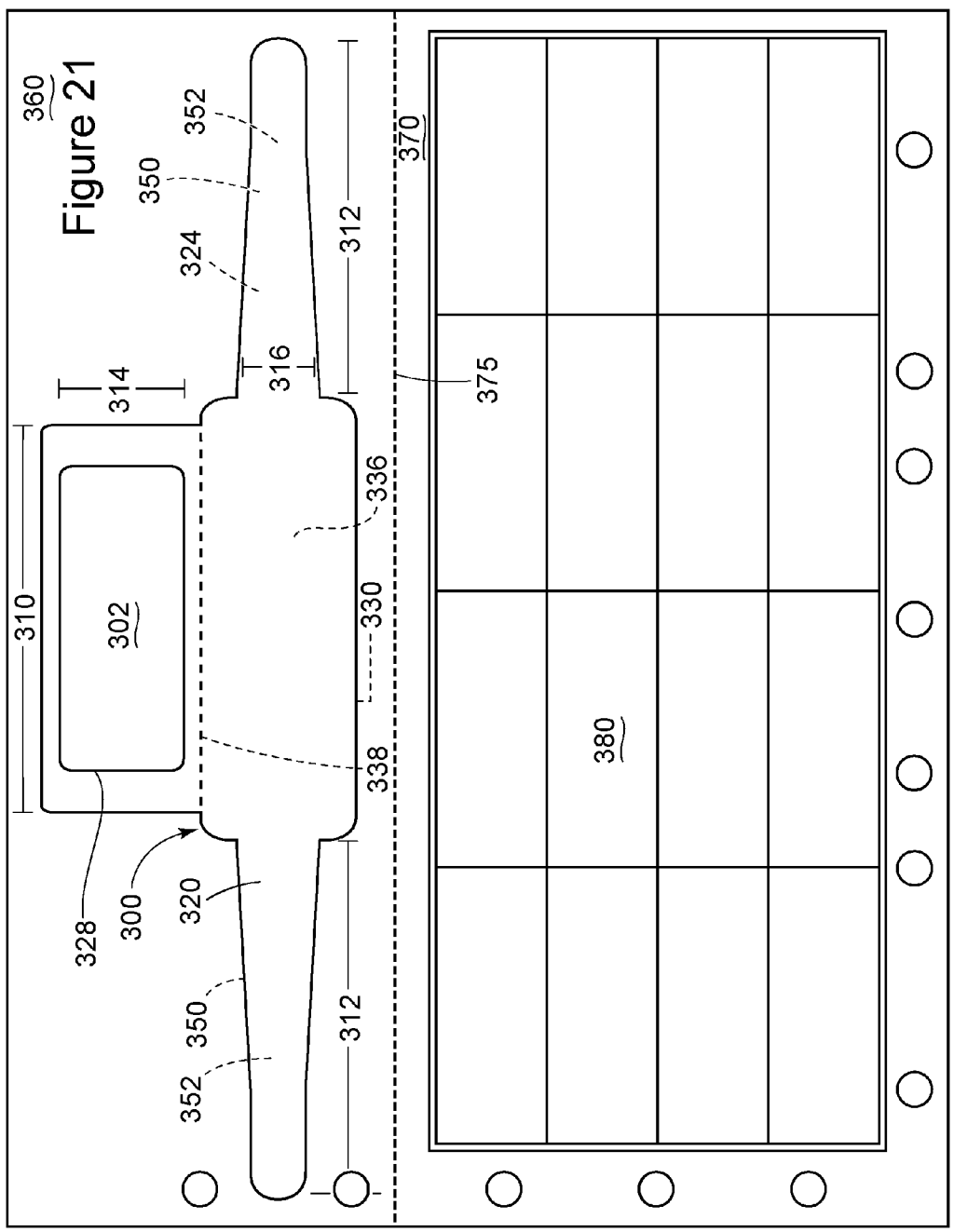
FIG. 21 is a top view of a page sized sheet form of the present invention having a wristband with an over-sized imaging area and a pair of narrow straps along with a matrix of labels.
Figure 22:
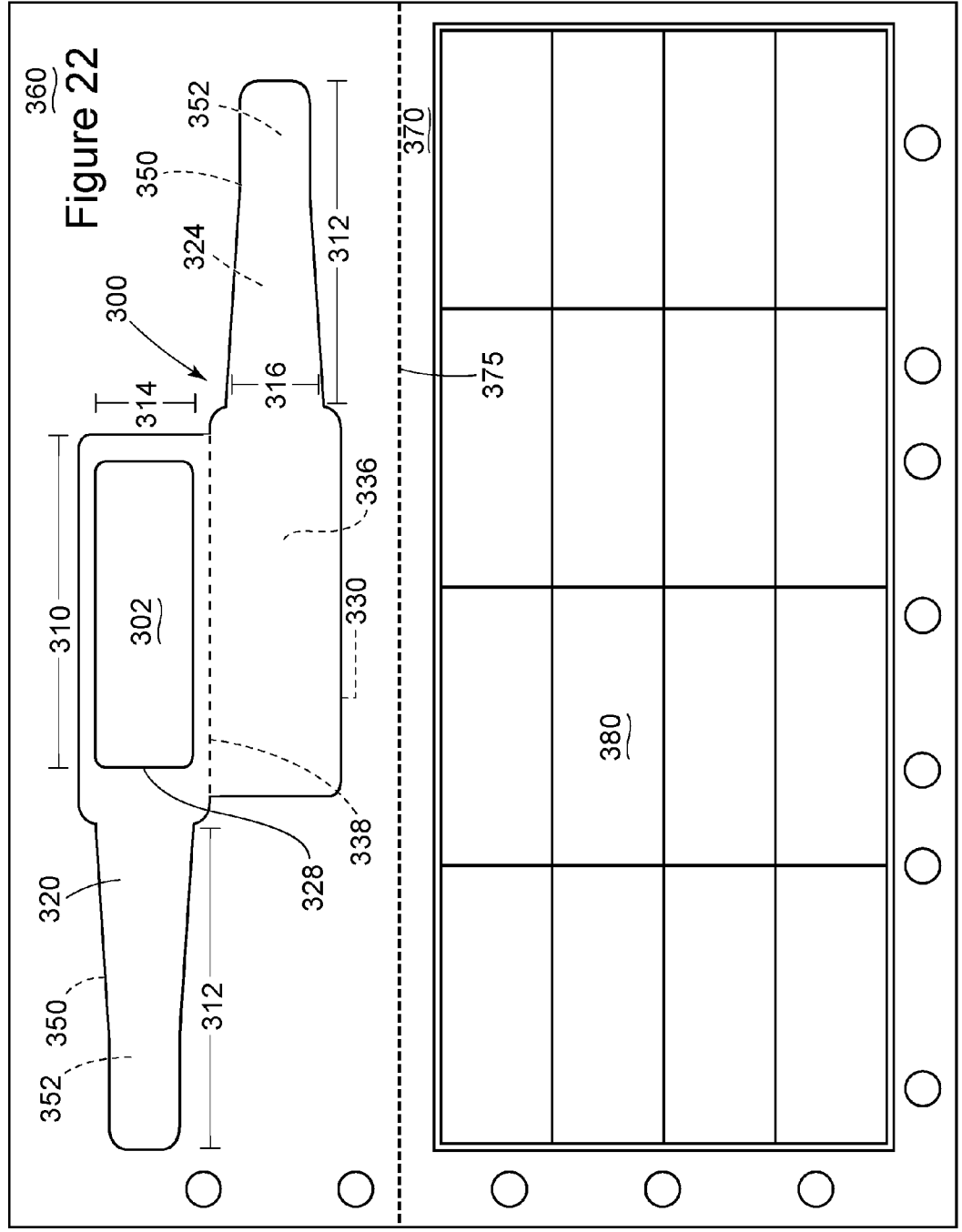
FIG. 22 is yet another embodiment of a wristband where the straps are in an offset arrangement in the lamination ply.

FIGS. 21 and 22 show embodiments of a business form of the present invention featuring a wristband 300 with differently sized print area 302. In both embodiments, a length 310 of the print area (comprised of face stock) is reduced to be substantially shorter than the overall length which includes two lengths 312 of the straps 352. More preferably, the length of the print area is less than the combined overall length of the two straps 352. Most preferably, the length of the print area is less than the length of either of the straps 352. It is noted in this embodiment that the print area 302, after the wristband is separated from the form and assembled, takes on the appearance of a "badge". By "badge" is meant that the width of the print area 302, with or without the laminate overlay, is wider than the straps 352. It is further noted that in this construction, the two straps 252 comprise a single ply or layer of laminate, thereby rendering them more pliable or flexible than multiple ply or layer straps.

A width 314 of the print area is preferably increased slightly over other embodiments to be wider than a width 316 of the straps so as to allow indicia to be printed transversely across the wristband. However, the print area width 314 is preferably, although not absolutely required to be, sized to maintain patient comfort and to generally retain a slender longitudinal profile for the wristband. The reduced length 310 of the print area 302 allows the print area 302 to be more naturally oriented on the top or bottom of a patient's wrist when the wristband 300 is secured around a patient's wrist. This in turn reduces the curvature of the print area 302, which in turn reduces the distortion of indicia printed on the print area 302 and facilitates automated reading thereof such as with a bar code reader (not shown).

As with other embodiments of the wristbands disclosed in the parent applications, the embodiments of the wristbands of FIGS. 21 and 22 also comprise two plies: a face ply 320 and a lamination ply 324. Preferably, the face ply has die cuts 328 defining the print area 302 for the wristband. The lamination ply preferably has die cuts 330 defining a laminating portion 336. Preferably, the laminating portion 336 is provided with a fold line 338 to facilitate folding the laminating portion over the face stock print area 302. Preferably, the laminating portion 336 overlies both the top and bottom of the print area to thereby totally encapsulate it. The print area 302 may be adhered to the lamination ply 324 such that when the wristband is removed from the form, the print area is retained on the lamination ply. To maximize the seal of the laminated wristband, the laminating portion is preferably provided with a periphery of adhesive 340 (FIG. 23) that surrounds the print area when the laminating portion is folded over the print area. To increase the visibility of information in the print area through the laminating portion, a central area of the laminating portion within the adhesive periphery may be provided with a release coating 342 (FIG. 23) instead of adhesive. This adhesive pattern thus forms a "window frame" effect to surround the face stock for sealing while eliminating any interposed layer of adhesive which might at least partially obscure the reading of any printed or imaged information including especially a bar code.

The lamination ply also has die cuts 350 defining a pair of straps 352. The straps are formed with adhesive patches 354 (FIG. 23) on their distal ends. Preferably, when the wristband is removed from the form, the adhesive patches are covered with a protective layer that may be removed when securing the wristband. In the embodiment shown in FIG. 21, the straps are formed on the same side of the fold line and in substantially the same horizontal plane with respect to the laminating portion. Thus, the adhesive patches are aligned on the same side when the wristband is secured around the patient's appendage. In other words, one strap may be adhered with its adhesive patch to the other strap and the adhesive patch on the other strap is simply folded over and adhered to its own strap to avoid any interference. As an alternative, the two straps may also be formed adjacent the print area and yet still be in substantially the same horizontal plane with respect to the laminating portion.

FIG. 22 shows another embodiment of the present invention where the straps are formed in an offset arrangement in the lamination ply. In this embodiment, one strap is formed adjacent the printable face stock area and the other strap is formed in the lamination ply adjacent the laminating portion, or in different horizontal planes with respect to the laminating portion. Thus, after separation and when the laminating portion is folded over the fold line to encapsulate the print area, the adhesive patches on the strap distal ends are aligned in a face to face arrangement when the wristband is wrapped around the patient's wrist. By adhering the adhesive patches together, the tensile strength of the wristband is increased thereby making the attachment more secure.

Figure 23:
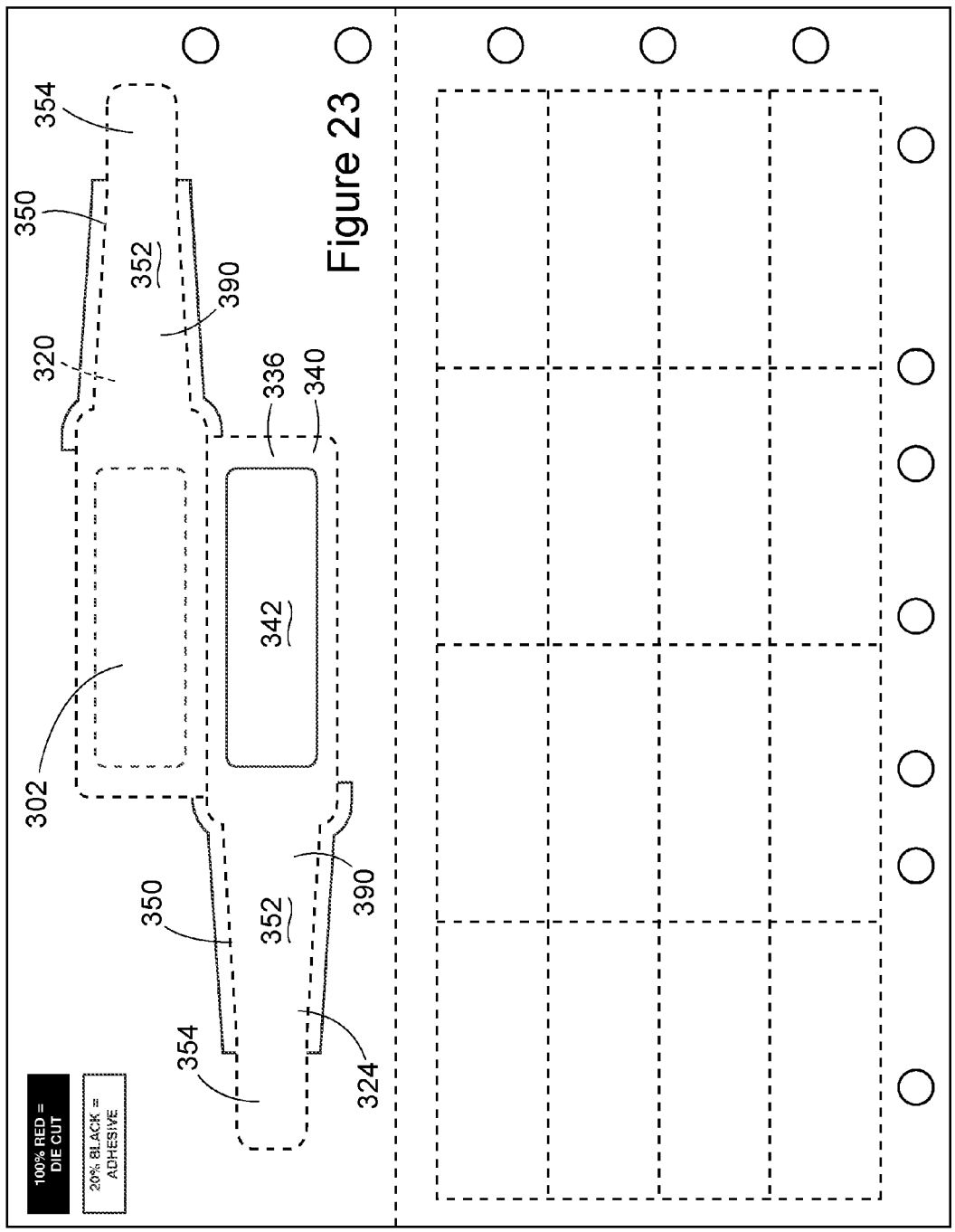
FIG. 23 is a bottom view of the form of FIG. 22 showing the arrangement of adhesive and release coatings applied to the wristband portion of the form.

Still another feature of the embodiments shown in FIGS. 21 and 22 is the shape of the panels comprising the laminating portion 336, and the layer of adhesive as shown in FIG. 23. As shown, one panel is shaped differently than the other, and importantly, the adhesive layer is applied to create the window frame effect with the generally rectangularly shaped portions that comprise the extent of the overlapping portions of the panels. In other words, in either embodiment, after the panels are overlapped, the adhesive joins the generally rectangularly shaped surround of the imaging area, leaving a curved, single layer shoulder transition area from the encapsulated imaging area to the straps. With this construction, upon assembly, the imaging area comprises three thicknesses of material: one face stock layer and two opposing and aligned laminating layers; transitioning to two thicknesses of material: two laminating layers adhered to each other and surrounding the imaging area in window frame fashion; transitioning to one thickness: the shaped, sloped shoulder portion of the panels which then flow into the narrower straps. After assembly and attachment to a patient, this construction provides a stepped down transition, from three layers to one layer, which provides not only enhanced patient comfort but also greater flexibility so as to enhance the "wearability" of the wristband. Further, by providing, in effect, a "hinge" comprising the shaped shoulder portion, less strain is imposed on the adhesively joined window frame as the patient moves so as to provide a better seal. This transition minimizes the bending imposed on the window frame, to the same effect. Even further, this construction creates a bend point intermediate the imaging area and the strap, so that any bending forces exerted on the wristband as it is worn first bend the shoulder transition to thereby at least partially insulate the imaging area from bending, thereby relieving stress on the imaging area and allowing it to remain flatter and more readily readable by a bar code or other automatic information reader seeking to read the imaging area.

In the wristband forms shown in FIGS. 21 and 22, the business form is preferably formed with a first portion 360 containing the wristband, and a second portion 370 separated from the first portion by a perforation line 375 that contains a plurality of self-adhering labels 380. As stated previously, the self adhering labels 380 may be used to match a patient to his or her belongings, medications, medical testing order forms or patient charts, etc. Preferably, the form is page-sized, such as for example 8½×11 inches, in a conventional size for ready processing through a conventional laser printer as a single sheet. Preferably, the first portion 360 of the form is envelope-sized. More preferably, the first portion 360 of the form has a dimension which approximates a number 10 sized envelope. This allows the first and second portions 360, 370 of the form to be separated at the perforation line 375 and the first or wristband portion 360 of the form to be processed through a standard laser printer through the envelope feeder, if for instance, the self-adhering labels are not immediately needed.

FIG. 23 provides additional detail of the arrangement of adhesive 340 and release coatings 342 applied to the laminating portion 336 and print area 302 of the wristband of FIG. 22. FIG. 23 also shows the arrangement of a release coating 390 applied along a portion of the length of each strap 352. The release coating 390 on the strap allows the wristband to be removed from the form with no face stock in the area between the laminating portion 336 and the adhesive patches 354, thereby resulting in a single ply strap which enhances patient comfort with less wristband material curving around the patient's appendage.

Figure 24:
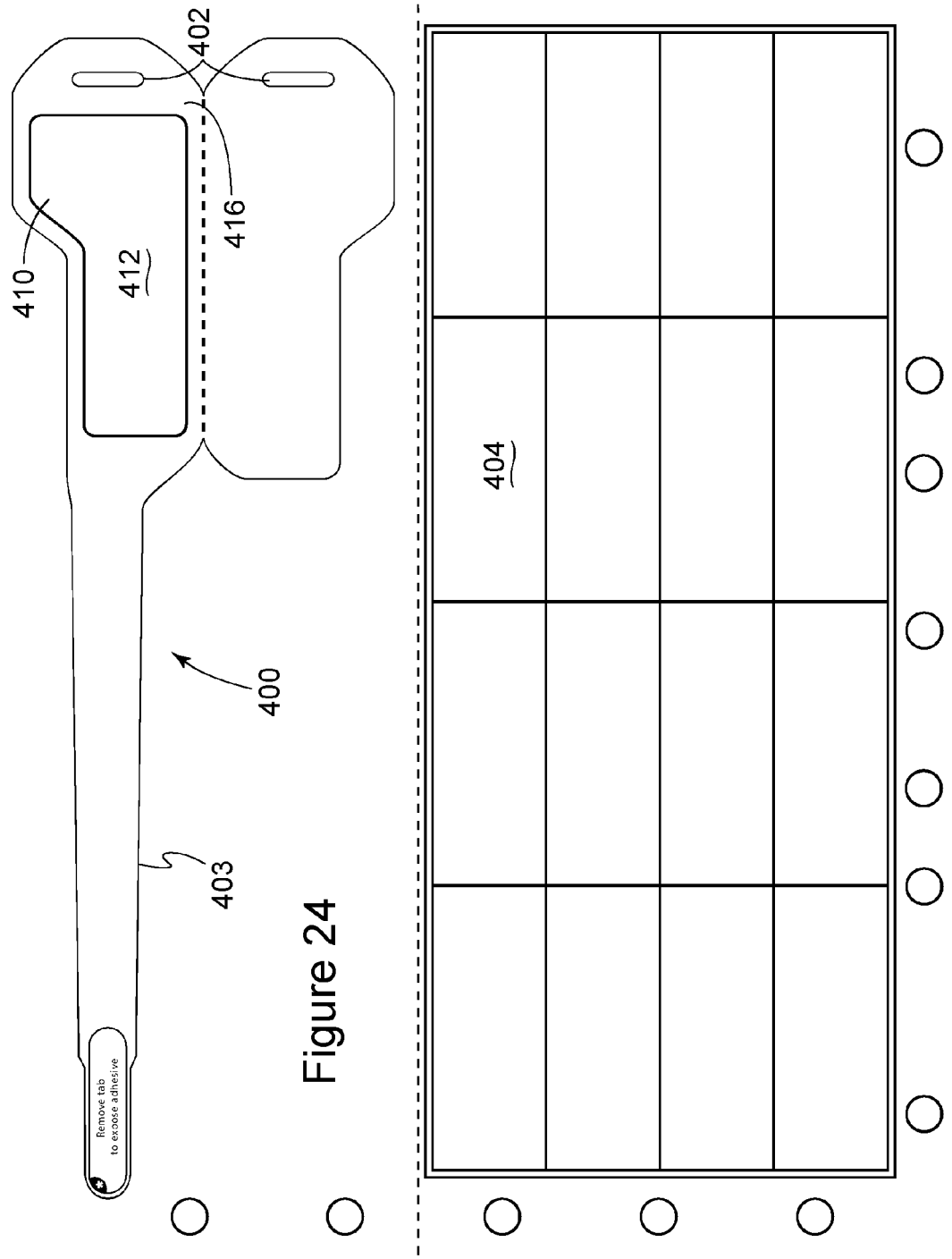
FIG. 24 is a top view of another embodiment of the business form of the present invention where the wristband has an irregularly sized print area with a print area tab formed adjacent one end and adjacent the cinch slot.

FIGS. 24 and 26 show yet another embodiment of the invention comprising a wristband 400 with a cinch slot 402, strap 403, and a plurality of self-adhering labels 404. As shown in FIGS. 24 and 26, a bulge 410 is formed along an outboard longitudinal side of the print area 412, which is mirrored in the laminating portions for covering and sealing the print area 412 after separation and assembly of the wristband 400. Preferably, the bulge 410 is provided adjacent the cinch slot 402 and an attachment portion 416 of the wristband. The bulge 410 extends outwardly and perpendicularly from the longitudinal axis of the print area 412 to form it into a bulged rectangular shape. A print area having a bulged rectangular shape is defined as a generally "rectangularly shaped" area having an enlarged portion of sufficient size along its edge to accommodate the printing of a ladder bar code of sufficient length as is typically required for a patient in a typical health care application. The to bulge portion 410 of imaging area 412 allows information such as a bar code to be printed in ladder fashion across the width of the wristband, as shown in FIG. 26. By printing information on the bulge portion 410, it becomes aligned with the length of the patient's arm instead of across the narrower width of the patient's wrist, thus allowing it to lie flatter against the patient as the wristband is worn. Furthermore, by having this data arranged vertically, a nurse or other health care professional need not turn the person's arm around as much to access it. Also, the more extreme curvature of smaller wrists, such as in many women and infants, does not cause the bulge portion to curve nearly as much as it would the length of the wristband. This facilitates reading and scanning the information while minimizing the overall size of the print area.

Yet another embodiment of the present invention is shown in FIG. 25 and comprises a wristband form used for a patient's blood collection and blood product compatibility. The wristband 500 is similar in nature to the wristbands disclosed in the parent applications but the form includes a plurality of self-adhering labels specially pre-printed for a patient's blood collection and blood products compatibility. By way of example and not in any limiting sense, when a patient is first treated by a healthcare provider, the wristband may be imprinted with a unique identifying bar code 510. Many, if not all, of the self-adhering labels may be imprinted with the same bar code to facilitate tracking and administering blood products. The form may be provided with a collection specimen label 512 to allow a patient's blood sample to be taken and the specimen to be tracked, for instance, in the laboratory to determine the patient's blood type and compatibility. Other labels 514 on the form may be used by healthcare providers to order blood products for an identified patient. The same form includes labels 516 that may be used by blood bank personnel to label the ordered blood products so that they may be easily matched to the identified patient. Other labels on the form may be used by the patient's health care providers to administer the ordered blood products 518, match them to the patient 520, and track units of blood given an identified patient 522.

Yet another novel and non-obvious feature is shown in the form depicted in FIGS. 25, 25A, 26 and 26A. That comprises the security seal 525. Security seal 525 comprises a relatively small patch die cut into the lamination layer of any of the foregoing embodiments and which can be applied over the sealing engagement of the strap, tabs, etc. as they are joined to secure the wristband to the patient. This provides a "seal down" over the attachment point of the wristband and another joinder as well as a protective layer to further guard against tampering or unintentional dis-lodging of the original attachment. In addition, preferably one or more die cuts, such as shown as X's in FIGS. 25A and 26A, may be formed to create points of weakness 527 in the security seal 525 and which are intended to likely cause separation, tearing or some other change in the appearance of the security seal should it be removed after application to serve as an indication that it has been tampered with by the patient. These points of weakness need not be X's, but instead need only be sufficient to create points of weakness that separate or otherwise exhibit tampering through at least partial removal thereof. To enhance the viewability of any tampering, the points of weakness may be surrounded by colored areas 529 to provide contrast from the generally colorless or transparent laminate layer from which the security seal patch is formed. These colored areas may be formed into regular polygonal shapes, such as the hexagon shapes shown, or otherwise be "regular" such that if a patient attempts to remove and re-apply the security seal he must further attempt to align these colored areas to cover up his tampering effort. This is difficult if not impossible to do even if extreme care is taken. Although preferably, as shown in the preferred embodiment, these colored areas surround the points of weakness, they may instead be placed to overlap, partially or completely, the points of weakness or otherwise be positioned with respect thereto.

The inventions have been disclosed herein in several embodiments with several alternatives to the construction of the wristband, as well as other inventive features and accessories. It will be appreciated by those of ordinary skill in the art that various alternatives not specifically mentioned are well within the scope of the these inventions. Some of these alternatives include the choice of specific materials for each layer of face stock or laminate, the particular adhesive used, and other details of construction for the page sized sheet in which the wristband is formed. The particular length or shape of the strap may be varied to adapt to the particular application, the location of the patch of adhesive at the end of the strap may be changed or eliminated, the point at which the strap extends from the laminating portion, and other arrangement details may also be considered as part of the invention. While it is considered as desirable by the inventor to not laminate the strap portion, there is no reason why it need not be laminated should the additional strength such an arrangement would provide be desired. Face stock shape or size may be changed, and to the tab may be separated from the imaging area, or located in a different position in the imaging area, and yet achieve a similar effect. The preferred embodiments disclosed herein are intended to be exemplary and not limiting as to the subject matter of the invention. Other similar, or different, changes will be contemplated and those changes are to be considered as part of this invention which should be limited only by the scope of the claims as appended hereto, and their legal equivalents.

What is claimed is:

1. A business form including a sheet with a separable wristband die cut therein, said sheet comprising a lamination ply and a face stock ply, the face stock ply having a die cut defining a wristband print area, the lamination ply having a die cut defining a wristband laminating portion, said laminating portion comprising a pair of offset panels with a pair of straps extending to their sides, at least one of said panels having an asymmetrical transition between it and the other of said panels, wherein the strap associated with the panel having the asymmetrical transition being substantially adhesive free along its length except for a patch of adhesive at its end, and a die cut in said face stock ply to define a protective layer of face stock covering said adhesive patch so that the wristband may be separated from the sheet by separating it at the protective layer.

2. The business form of claim 1 wherein said asymmetrical transition comprises a curvilinear transition.

3. The business form of claim 1 wherein said asymmetrical transition comprises a non-orthogonal transition.

4. The business form of claim 1 wherein said asymmetrical transition comprises a shoulder extending between it and the strap extending therefrom.

5. The business form of claim 1 further comprising a plurality of self adhering labels die cut therein.

6. A business form including a sheet with a separable wristband, said sheet comprising a lamination ply and a face stock ply, the face stock ply having a die cut defining a wristband print area, the lamination ply having a die cut defining a wristband laminating portion comprising a pair of panels with a pair of straps extending to their sides, wherein at least one of said panels has an offset shoulder transition between at least it and the other of said panels to facilitate separation of said wristband from said sheet while maintaining the integrity of said laminating portion, wherein the strap associated with the panel having the offset shoulder transition being substantially adhesive free along its length except for a patch of adhesive at its end, and a die cut in said face stock ply to define a protective layer of face stock covering said adhesive patch so that the wristband may be separated from the sheet by separating it at the protective layer.

7. The business form of claim 6 wherein said offset shoulder transition extends outboard of the other panel's corresponding end.

8. The business form of claim 7 further comprising a fold line between said pair of panels, said fold line aligned with and extending substantially to an end of the offset shoulder transition.

9. The business form of claim 8 wherein each of said panels has an offset shoulder transition, said offset shoulder transitions extending between it and its associated strap.

10. The business form of claim 6 wherein the panel end adjacent the offset shoulder transition has a substantially straight edge leading into said offset shoulder transition, said straight edge partially forming a periphery for surrounding the print area upon separation and folding over of said panels to substantially encapsulate said print area.

11. The business form of claim 10 wherein said offset shoulder transition is substantially devoid of adhesive.

12. The business form of claim 6 wherein an offset shoulder transition is situated between each strap and its corresponding panel.

13. The business form of claim 12 wherein one of said offset shoulder transitions is situated between each of said straps and the same panel.

14. The business form of claim 12 wherein one of said offset shoulder transitions is between each of said straps and a different one of said panels.

15. The business form of claim 6 wherein each panel has a second shoulder at the same end as an offset shoulder transition, said panel ends being at opposite ends of the print area.

16. The business form of claim 6 wherein the panel adjacent the offset shoulder transition has a substantially straight edge leading into said offset shoulder transition.

17. The business form of claim 16 further comprising a fold line between said pair of panels, said fold line aligned with and extending substantially to an end of the offset shoulder transition.

18. The business form of claim 17 wherein said straps extend to the sides of only one of said panels and further comprising one of said offset shoulder transitions at both ends of said panel.

19. The business form of claim 17 wherein each of said straps extend to the side of a different one of said panels and further comprising one of said offset shoulder transitions between each of said straps and its associated panel.

20. The business form of claim 6 further comprising a plurality of self adhering labels die cut therein.

21. A business form including a sheet with a separable wristband, said sheet comprising a lamination ply and a face stock ply, the face stock ply having a die cut defining a wristband print area, the lamination ply having a die cut defining a wristband laminating portion, said laminating portion comprising a pair of panels with straps extending to their sides, said print area being adhered to one of said panels, at least one of said panels having an overlapping end so that when the wristband is separated from the sheet and the panels are folded over to laminate the print area, said panel end overlaps the other panel's corresponding end, the strap associated with the panel having the overlapping end being substantially adhesive free along its length except for a patch of adhesive at its end, and a die cut in said face stock ply to define a protective layer of face stock covering said adhesive patch so that the wristband may be separated from the sheet by separating it at the protective layer.

22. The business form of claim 21 wherein one of said straps extends to the side of said offset end.

23. The business form of claim 22 wherein said overlapping end is curvilinear.

24. The business form of claim 23 wherein each of said panels has an overlapping end with a strap extending therefrom.

25. The business form of claim 24 wherein the panel adjacent the overlapping end has a substantially straight edge leading into said overlapping edge.

26. The business form of claim 25 wherein each of said overlapping ends is a shaped shoulder situated between each panel end and its associated strap.

27. The business form of claim 21 further comprising a plurality of self adhering labels die cut therein.

28. A business form including a sheet with a separable wristband carrier die cut therein, said sheet comprising at least a lamination ply, the lamination ply having a die cut defining a wristband laminating portion, said wristband laminating portion comprising a pair of offset panels with a pair of straps extending to their sides, said offset panels being sufficiently offset so that upon folding them over to laminate them, each of said panels has an exposed edge, and at least one of said panels having an asymmetrical transition between it and the other of said panels, each of said straps being substantially adhesive free along their length except for a patch of adhesive at their ends.

29. The business form of claim 28 wherein said asymmetrical transition comprises a curvilinear transition.

30. The business form of claim 28 wherein said asymmetrical transition comprises a non-orthogonal transition.

31. The business form of claim 28 wherein said asymmetrical transition comprises a shoulder extending between it and the strap extending therefrom.

32. The business form of claim 28 further comprising a plurality of self adhering labels die cut therein.

33. A business form including a sheet comprising at least a lamination ply, the lamination ply having a die cut defining a wristband laminating portion comprising a pair of panels with a pair of straps extending to their sides, and wherein at least one of said panels has an offset shoulder transition between at least it and the other of said panels to facilitate separation of said lamination portion from said sheet while maintaining its integrity, said offset shoulder transition extending outboard of the other panel's corresponding end, and each of said straps being substantially adhesive free along their length except for a patch of adhesive at their ends.

34. The business form of claim 33 further comprising a fold line between said pair of panels, said fold line aligned with and extending substantially to an end of the at least one offset shoulder transition.

35. The business form of claim 34 wherein each of said panels has an offset shoulder transition, each of said offset shoulder transitions extending between it and its associated strap.

36. The business form of claim 33 wherein at least the strap associated with the at least one offset shoulder transition is substantially adhesive free along its length except for a patch of adhesive at said end.

37. The business form of claim 33 wherein an offset shoulder transition is situated between each strap and its corresponding panel.

38. The business form of claim 37 wherein one of said offset shoulder transitions is situated between each of said straps and the same panel.

39. The business form of claim 37 wherein one of said offset shoulder transitions is situated between each of said straps and a different one of said panels.

40. The business form of claim 33 wherein each panel has a second shoulder at the same end as an offset shoulder transition, said panel ends being at opposite ends.

41. The business form of claim 33 wherein the panel adjacent the offset shoulder transition has a substantially straight edge leading into said offset shoulder transition.

42. The business form of claim 41 further comprising a fold line between said pair of panels, said fold line aligned with and extending substantially to an end of the offset shoulder transition.

43. The business form of claim 42 wherein said straps extend to the sides of only one of said panels and further comprising one of said offset shoulder transitions at both ends of said panel.

44. The business form of claim 42 wherein each of said straps extend to the side of a different one of said panels and further comprising one of said offset shoulder transitions between each of said straps and its associated panel.

45. The business form of claim 44 wherein each strap is substantially adhesive free along its length except for a patch of adhesive at its end.

46. The business form of claim 33 further comprising a plurality of self adhering labels die cut therein.

47. A business form including a sheet comprising at least a lamination ply, the lamination ply having a die cut defining a wristband laminating portion comprising a pair of panels with a pair of straps extending to their sides, and wherein at least one of said panels has an offset shoulder transition between at least it and the other of said panels to facilitate separation of said lamination portion from said sheet while maintaining its integrity, each of said straps being substantially adhesive free along their length except for a patch of adhesive at their ends and wherein the panel end adjacent the at least one offset shoulder transition has a substantially straight edge leading into said at least one offset shoulder transition, said straight edge partially forming a periphery for surrounding a print area upon separation and folding over of said panels to substantially encapsulate said print area.

48. The business form of claim 47 wherein said at least one offset shoulder transition is substantially devoid of adhesive.

49. A business form including a sheet comprising at least a lamination ply, the lamination ply having a die cut defining a wristband laminating portion, said laminating portion comprising a pair of panels with straps extending to their sides, and at least one of said panels having an overlapping end so that when the wristband laminating portion is separated from the sheet and the panels are folded over to laminate a print area, said panel end overlaps the other panel's corresponding end, each of said straps being substantially adhesive free along their length except for a patch of adhesive at their ends.

50. The business form of claim 49 wherein one of said straps extends to the side of said offset end.

51. The business form of claim 50 wherein said at least one overlapping end is curvilinear.

52. The business form of claim 51 wherein each of said panels has an overlapping end with a strap extending therefrom.

53. The business form of claim 52 wherein the panel adjacent the overlapping end has a substantially straight edge leading into said overlapping edge.

54. The business form of claim 53 wherein each of said overlapping ends is a shaped shoulder situated between each panel end and its associated strap.

55. The business form of claim 49 further comprising a plurality of self adhering labels die cut therein.

* * * * *